United States Patent

Fujioka et al.

Patent Number: 5,198,448
Date of Patent: * Mar. 30, 1993

[54] CARDIOTONICS

[75] Inventors: Takafumi Fujioka, Itano; Shuji Teramoto, Tokushima; Michiaki Tominaga, Itano; Yoichi Yabuuchi, Tokushima, all of Japan

[73] Assignee: Otsuka Pharmaceutical Company, Limited, Tokyo, Japan

[*] Notice: The portion of the term of this patent subsequent to Oct. 1, 2008 has been disclaimed.

[21] Appl. No.: 734,957

[22] Filed: Jul. 24, 1991

Related U.S. Application Data

[62] Division of Ser. No. 391,305, Aug. 9, 1989, Pat. No. 5,053,514.

[30] Foreign Application Priority Data

Aug. 10, 1988 [JP]  Japan .................. 63-200929
Feb. 14, 1989 [JP]  Japan .................. 1-34688
Jun. 21, 1989 [JP]  Japan .................. 1-160170

[51] Int. Cl.$^5$ .................. C07D 215/227
[52] U.S. Cl. .................. 514/312; 546/157
[58] Field of Search .................. 514/312; 546/157

[56] References Cited

U.S. PATENT DOCUMENTS

| | | | |
|---|---|---|---|
| 4,210,753 | 7/1980 | Tominaga et al. | 546/157 |
| 4,309,432 | 1/1982 | Tanaka et al. | 514/312 |
| 4,652,672 | 3/1987 | Linder | 548/444 |
| 4,914,093 | 4/1990 | Morisawa et al. | 544/238 |
| 5,015,638 | 5/1991 | Spada et al. | 514/211 |
| 5,053,514 | 10/1991 | Fujioka et al. | 546/157 |

FOREIGN PATENT DOCUMENTS

| | | | |
|---|---|---|---|
| 15505 | 9/1980 | European Pat. Off. | 514/312 |
| 4951271 | 9/1972 | Japan | 546/157 |
| 568319 | 1/1981 | Japan | 514/312 |
| 1058822 | 2/1967 | United Kingdom | 546/157 |

*Primary Examiner*—Robert T. Bond
*Assistant Examiner*—E. C. Ward
*Attorney, Agent, or Firm*—Wegner, Cantor, Mueller & Player

[57] ABSTRACT

Method for prophylaxis and treatment of heart diseases using a carbostyril derivative of formula:

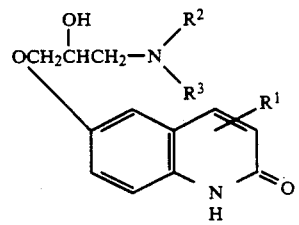

wherein $R^1$ is H or CN, and $R^2$ and $R^3$ are each H, alkyl optionally substituted by OH, cycloalkyl, alkenyl, phenyl, phenylalkyl having optionally substituents of alkoxyalkoxy, halogen, alkoxy, $NO_2$, alkyl, CN, alkylthio or alkylsulfinyl on phenyl ring and having optionally OH-substituent on alkyl moiety, phenylsulfonylalkyl having optionally alkoxy substituent on phenyl ring, phenylthioalkyl, phenylsulfinylalkyl having optionally substituents of halogen or alkoxy on phenyl ring, phenoxyalkyl having optionally substituents of halogen or alkoxy on phenyl ring, pyridylalkyl having optionally substituents of halogen or alkoxy on pyridine ring, thienylalkyl, benzoylalkyl, anilinothiocarbonyl, benzoyl, pyridyl, phenylalkenyl, or group of $-A-NR^4R^5$ ($R^4$ and $R^5$ are each alkyl or phenyl having optionally substituents of halogen or alkoxy on phenyl ring, and A is alkylene which may be interrupted with O), and a salt thereof, and novel carbostyril derivatives, and pharmaceutical composition for prophylaxis and treatment of heart diseases containing said novel carbostyril derivative.

15 Claims, No Drawings

CARDIOTONICS

This application is a divisional of Ser. No. 07/391,305, filed Aug. 9, 1989, now U.S. Pat. No. 5,053,514.

This invention relates to a cardiotonic agent comprising as an active ingredient a carbostyril derivative or a pharmaceutically acceptable salt thereof, novel carbostyril derivatives, and processes for preparing the same. More particularly, it relates to a cardiotonic agent comprising as an active ingredient a carbostyril derivative of the formula:

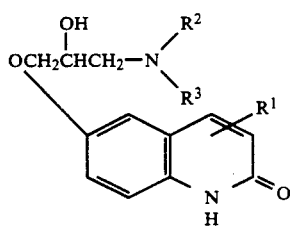

wherein $R^1$ is hydrogen atom or cyano group, and $R^2$ and $R^3$ are the same or different and are each hydrogen atom, a lower alkyl group being optionally substituted by hydroxy group, a cycloalkyl group, a lower alkenyl group, a phenyl group, a phenyl(lower)alkyl group which has optionally 1 to 3 substituents selected from the group consisting of a lower alkoxy(lower)alkoxy group, a halogen atom, a lower alkoxy group, a nitro group, a lower alkyl group, a cyano group, a lower alkylthio group and a lower alkylsulfinyl group on the phenyl ring and further has optionally a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(lower)alkyl group having optionally 1 to 3 substituents selected from the group consisting of a halogen atom and a lower alkoxy group on the phenyl ring, a phenoxy(lower)alkyl group having optionally 1 to 3 substituents selected from the group consisting of a halogen atom and a lower alkoxy group on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula:

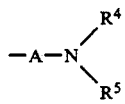

(wherein $R^4$ and $R^5$ are the same or different and are each a lower alkyl group or a phenyl group having optionally 1 to 3 substituents selected from the group consisting of a halogen atom and a lower alkoxy group on the phenyl ring, and A is a lower alkylene group which may optionally be interrupted an with oxo group), and a pharmaceutically acceptable salt thereof.

This invention also relates novel carbostyril derivatives of the formula:

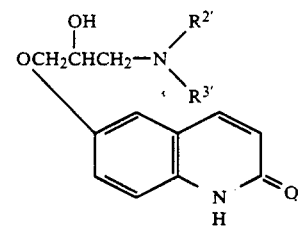

wherein
$R^{2'}$ is hydrogen atom, a lower alkyl group being optionally substituted by hydroxy group, a cycloalkyl group, a lower alkenyl group, a phenyl group, a phenyl(lower)alkyl group which has optionally 1 to 3 substituents selected from the group consisting of a lower alkoxy(lower)alkoxy group, a halogen atom, a lower alkoxy group, a nitro group, a lower alkyl group, a cyano group, a lower alkylthio group and a lower alkylsulfinyl group on the phenyl ring and further has optionally a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(lower)alkyl group having optionally 1 to 3 substituents selected from the group consisting of a halogen atom and a lower alkoxy group on the phenyl ring, a phenoxy(lower)alkyl group having optionally 1 to 3 substituents selected from the group consisting of a halogen atom and a lower alkoxy group on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula:

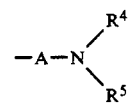

(wherein $R^4$ and $R^5$ are the same or different and are each a lower alkyl group or a phenyl group having optionally 1 to 3 substituents selected from the group consisting of a halogen atom and a lower alkoxy group on the phenyl ring, and A is a lower alkylene group which may optionally be interrupted with an oxo group), and $R^{3'}$ is a phenyl(lower)alkyl group which has a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(lower)alkyl group having optionally 1 to 3 substituents selected from the group consisting of a halogen atom and a lower alkoxy group on the phenyl ring, a phenoxy(lower)alkyl group having 1 to 3 substituents of a halogen atom on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula:

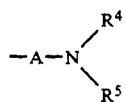

(wherein $R^4$, $R^5$ and A are the same as defined above, and a pharmaceutically acceptable salt thereof, and novel carbostyril derivatives of the above formula (II) wherein $R^{2'}$ is a lower alkyl group having a hydroxy substituent, and $R^{3'}$ is a phenyl(lower)alkyl group having 1 to 3 substituents selected from the group consisting of a lower alkoxy(lower)alkoxy group, a halogen atom, a nitro group, a lower alkyl group, a cyano group, a lower alkylthio group and a lower alkylsulfinyl group, and a pharmaceutically acceptable acid addition salt thereof, and further novel carbostyril derivatives of the formula:

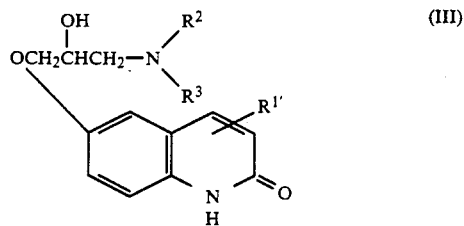

(III)

wherein $R^{1'}$ is cyano group, and $R^2$ and $R^3$ are the same as defined above, and a pharmaceutically acceptable salt thereof.

Prior Art

There have been known various carbostyril derivatives having various pharmacological activities. For example, Japanese Patent First Publication (Kokai) No. 80322/2982 discloses carbostyril derivatives of the formula:

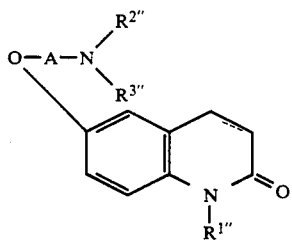

wherein $R^{1''}$ is hydrogen atom, a lower alkyl group or a phenyl(lower)alkyl group, and $R^{2''}$ and $R^{3''}$ are each hydrogen atom, a lower alkyl group being optionally substituted by hydroxy group, a cycloalkyl group, a phenyl(lower)alkyl group which has optionally 1 to 3 substituents selected from the group consisting of a lower alkoxy group, a halogen atom and a nitro group, or a phenoxy(lower)alkyl group having optionally a lower alkoxy substituent on the phenyl ring, or $R^{2''}$ and $R^{3''}$ combine together with nitrogen atom to which they bond with or without being interrupted with other nitrogen atom or oxygen atom to form a 5- or 6-membered heterocyclic group, said heterocyclic group having optionally a substituent selected from a phenyl group, a lower alkyl group having optionally hydroxy substituent, or a phenyl(lower)alkyl group, and A is a lower alkylene group, and the carbon-carbon bond between 3- and 4-positions in the carbostyril nucleus being single bond or double bond, and a salt thereof, which is useful as a cardiotonic agent. These carbostyril derivatives are different from the compounds in the present invention in that they have no hydroxy group on the alkylene group of the group A.

Japanese Patent First Publication (Kokai) No. 8319/1981 discloses carbostyril derivatives of the formula:

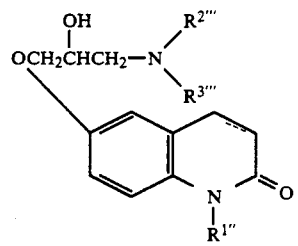

wherein $R''$ is hydrogen atom, a lower alkyl group, or a phenylalkyl group, $R^{2'''}$ is a phenyl group, a phenylalkyl group, a hydroxyalkyl group, a lower alkenyl group, a cycloalkyl group, or a phenoxyalkyl group, and $R^{3'''}$ is hydrogen atom, a lower alkyl group, a lower alkenyl group, a cycloalkyl group, a phenyl group, or a phenylalkyl group, or $R^{2'''}$ and $R^{3'''}$ combine together with nitrogen atom to which they bond with or without being interrupted with other nitrogen atom or oxygen atom to form a 5- or 6-membered saturated heterocyclic group, and the carbon-carbon bond between 3- and 4-positions in the carbostyril nucleus being single bond or double bond, and a salt thereof, which is useful as an antihistaminic agent. In this reference, it is also disclosed that it is known that some of the carbostyril derivatives have $\beta$-adrenergic blocking activity and are useful as a medicament for the treatment of arrhythmia and angina pectoris. The carbostyril derivatives of this reference include some of the compound of the formula (I) of this invention, but this reference does not teach the use of the compounds as cardiotonics.

Japanese Patent First Publication (Kokai) No. 129268/1980 discloses carbostyril derivatives of the formula:

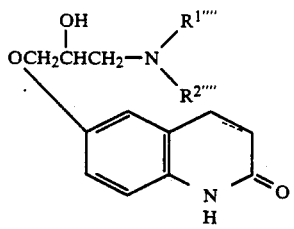

wherein $R^{1''''}$ is a lower alkenyl group or a phenyl group, and $R^{2''''}$ is hydrogen atom, a lower alkenyl group or a lower alkyl group, and the carbon-carbon bond between 3- and 4-positions in the carbostyril nucleus being single bond or double bond, and a salt thereof, which have central nervous system depressing activities and antihistaminic activity and are useful as a pre-anaesthetic agent, hypnosis inducing agent, a central muscle relaxant, a predrug for operation, an antischizophrenic agent, a sedative, a tranquilizer, an antidepressant, an antihistaminic, and the like. The carbostyril derivatives of this reference include the compounds of the formula (I) of this invention, too, but this reference does not teach the use of the compounds as cardiotonics, either.

European Patent Publication No. 15,505 discloses 3-amino-1,2-propanediol 1-aryl ether derivatives of the formula:

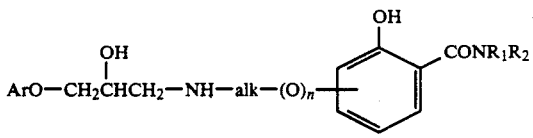

wherein Ar is an optionally substituted aryl including heteroaryl, n is 0 or 1, alk is $C_2$–$C_5$ alkylene, and $R^1$ and $R_2$ are each hydrogen atom or a lower alkyl, or they together form a lower alkylene optionally interrupted by O, S, N or N-lower alkyl, which is useful as β-adrenergic blockers or stimulants for treating cardiac disorders. The compounds of this reference are different from the compounds of the formula (I) of this invention in the substituent on the amino group.

British Patent 2,163,150 discloses also 3-aminopropoxy aromatic compounds having cardiotonic, antiarrhythmic, adrenergic receptor blocking and calcium antagonist properties, and the compounds of this reference include also some carbostyril derivatives similar to the compounds of this invention, but they are different from the compounds of this invention in the substituents on the hydroxypropylene chain.

British Patents 1,058,822 and 1,424,571, U.S. Pat. No. 4,652,672 and European Patent Publication 50,885 disclose also some carbostyril derivatives which may include some of the compounds of the formula (I) of this invention, but they are useful as β-adrenergic blockers.

European Patent Publication 255,134, and U.S. Pat. Nos. 4,514,401, 3,975,391, 3,994,901, 4,022,776, 4,022,784, 4,068,076, 4,145,542, and 4,026,897 disclose also some carbostyril derivatives which are useful as bronchodilators, vasodilators, antihypertensives, or cariotonics, but the compounds of these references are different from the compounds of this invention in the substituents on the carbostyril nucleus.

BRIEF DESCRIPTION OF THE INVENTION

The present inventors have extensively studied numerous carbostyril derivatives and the pharmacological activities thereof and have found that the carbostyril derivatives of the formulae (I), (II) and (III) show myocardial contraction increasing activity (i.e. positive inotropic activity), coronary blood flow increasing activity, hypotensive activity, an activity of inhibiting blood vessel contraction induced by norepinephrine, and antiinflamatory activity and are useful as cardiotonics for the treatment of heart diseases such as congestive heart failure, mitral valve disorders, atrial fibrillation, flutter, paroxysmal atrial frequent pulse, etc., hypotensives and inflammatory agents, and that these compounds are characteristic in that they show little effect of increasing heart rate notwithstanding their excellent positive inotropic, coronary blood flow increasing and hypotensive activities, and further that these compounds have low toxicity, less side effects on the central nervous system, for example less vomiting, less hypokinesis, less spasm and less tremor and further characteristic in excellent absorbability with excellent duration of the activities.

An object of the invention is to provide a cardiotonic agent comprising as an active ingredient a carbostyril derivative of the formula (I), formula (II) or formula (III), or a pharmaceutically acceptable salt thereof which is useful for the prophylaxis and treatment of heart diseases. Another object of the invention is to provide a novel carbostyril derivative of the formula (II) or formula (III) and a pharmaceutically acceptable salts thereof which has excellent cardiotonic activities. A further object of the invention is to provide a pharmaceutical composition for the prophylaxis and treatment of heart diseases which comprises as an active ingredient the carbostyril derivative of the formula (II) or formula (III), or a pharmaceutically acceptable salt thereof Still further object of the invention is to provide a process for preparing the carbostyril derivatives of the formula (II) or formula (III) or pharmaceutically acceptable salts thereof. These and other objects and advantages of the invention will be apparent to those skilled in the art from the following description.

DETAILED DESCRIPTION OF THE INVENTION

In the carbostyril derivatives of the formulae (I), (II) and (III) in this invention, the groups of $R^1$, $R^{1'}$, $R^2$, $R^{2'}$, $R^3$, $R^{3'}$, $R^4$, $R^5$ and A include specifically the following groups.

The lower alkyl group being optionally substituted by hydroxy group includes a straight chain or branched chain alkyl group having 1 to 6 carbon atoms which is optionally substituted by hydroxy group, for example, methyl, ethyl, propyl, isopropyl, butyl, tert-butyl, pentyl, hexyl, hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl, and the like.

The lower alkenyl group includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The halogen atom includes a fluorine atom, chlorine atom, bromine atom and iodine atom.

The lower alkoxy group includes a straight chain or branched chain alkoxy group having 1 to 6 carbon atoms, for example, methoxy, ethoxy, propoxy, isopropoxy, butoxy, tert-butoxy, pentyloxy, hexyloxy, and the like.

The lower alkyl group includes a straight chain or branched chain alkyl group having 1 to 6 carbon atoms, for example, methyl, ethyl, propyl, isopropyl, butyl, tert-butyl, pentyl, hexyl, and the like.

The lower alkylthio group includes a straight chain or branched chain alkylthio group having 1 to 6 carbon atoms, for example, methylthio, ethylthio, propylthio, isopropylthio, butylthio, pentylthio, hexylthio, and the like.

The lower alkylsulfinyl group includes a straight chain or branched chain alkylsulfinyl group having 1 to 6 carbon atoms, for example, methylsulfinyl, ethylsulfinyl, propylsulfinyl, isopropylsulfinyl, butylsulfinyl, pentylsulfinyl, hexylsulfinyl, and the like.

The lower alkylenedioxy group includes a straight chain or branched chain alkylenedioxy group having 1 to 4 carbon atoms, for example, methylenedioxy, ethylenedioxy, trimethylenedioxy, tetramethylenedioxy, and the like.

The phenyl(lower)alkyl group which has optionally 1 to 3 substituents selected from the group consisting of a lower alkoxy(lower)alkoxy group, a halogen atom, a lower alkoxy group, a nitro group, a lower alkyl group, a cyano group, a lower alkylthio group and a lower alkylsulfinyl group on the phenyl ring and further has optionally a hydroxy substituent on the alkyl moiety includes a phenylalkyl group wherein the alkyl moiety is a straight chain or branched chain alkyl group having 1 to 6 carbon atoms and having optionally a hydroxy substituent and further the phenyl ring has optionally 1 to 3 substituents selected from the group consisting of an alkoxyalkoxy group wherein each alkoxy moiety is a straight chain or branched chain alkoxy group having 1 to 6 carbon atoms, a halogen atom, a straight chain or branched chain alkoxy group having 1 to 6 carbon atoms, a nitro group, a straight chain or branched chain alkyl group having 1 to 6 carbon atoms, a cyano group, a straight chain or branched chain alkylthio group having 1 to 6 carbon atoms, and a straight chain or branched chain alkylsulfinyl group having 1 to 6 carbon atoms, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, diphenylmethyl, 2,2-diphenylethyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl, 2-(3-methylphenyl)ethyl, 1-(4-methylphenyl)ethyl, 2-methylbenzyl, 3-(2-ethylphenyl)propyl, 4-(3-ethylphenyl)butyl, 1,1-dimethyl-2-(4-ethylphenyl)ethyl, 5-(4-isopropylphenyl)pentyl, 6-(4-hexylphenyl)hexyl, 3,4-dimethylbenzyl, 3,4,5-trimethylbenzyl, 2,5-dimethylbenzyl, 2-(3-methylthiophenyl)ethyl, 1-(4-methylthiophenyl)ethyl, 2-methylthiobenzyl, 3-(2-ethylthiophenyl)propyl, 4-(3-ethylthiophenyl)butyl, 1,1-dimethyl-2-(4-ethylthiophenyl)ethyl, 5-(4-isopropylthiophenyl)pentyl, 6-(4-hexylthiophenyl)hexyl, 3,4-dimethylthiobenzyl, 3,4,5-trimethylthiobenzyl, 2,5-dimethylthiobenzyl, 2-(3-methylsulfinylphenyl)ethyl, 1-(4-methylsulfinylphenyl)propyl, 2-methylsulfinylbenzyl, 3-(2-ethylsulfinylphenyl)propyl, 4-(3-ethylsulfinylphenyl)butyl, 1,1-dimethyl-2-(4-ethylsulfinylphenyl)ethyl, 5-(4-isopropylsulfinylphenyl)pentyl, 6-(4-hexylsulfinylphenyl)hexyl, 3,4-dimethylsulfinylbenzyl, 3,4,5-trimethylsulfinylbenzyl, 2,5-dimethylsulfinylbenzyl, 4-cyanobenzyl, 2-(3-cyanophenyl)ethyl, 1-(2-cyanophenyl)ethyl, 3-(2-cyanophenyl)propyl, 4-(3-cyanophenyl)butyl, 1,1-dimethyl-2-(4-cyanophenyl)ethyl, 5-(4-cyanophenyl)pentyl, 6-(4-cyanophenyl)hexyl, 3,4-dicyanobenzyl, 3,4,5-tricyanobenzyl, 2,5-dicyanobenzyl, 2-chlorobenzyl, 2-(3-bromophenyl)ethyl, 1-(4-chlorophenyl)ethyl, 3-(4-fluorophenyl)propyl, 4-(2,3-dichlorophenyl)butyl, 1,1-dimethyl-2-(2,4-dibromophenyl)ethyl, 5-(3,4-difluorophenyl)pentyl, 6-(2,4,6-trichlorophenyl)hexyl, 2-methyl-3-(2-fluorophenyl)propyl, 2-(3-methoxymethoxyphenyl)ethyl, 1-(4-methoxymethoxyphenyl)ethyl, 2-methoxymethoxybenzyl, 3-[2-(2-methoxyethoxy)phenyl]propyl, 4-[3-(3-propoxypropoxy)phenyl]butyl, 1,1-dimethyl-2-[4-(4-butoxybutoxy)phenyl]ethyl, 5-[4-(5-pentyloxypentyloxy)phenyl]pentyl, 6-[4-(6-hexyloxyhexyloxy)phenyl]hexyl, 3,4-dimethoxymethoxybenzyl, 3,4,5-trimethoxymethoxybenzyl, 2,5-dimethoxymethoxybenzyl, 2-nitrobenzyl, 2-(3-nitrophenyl)ethyl, 1-(4-nitrophenyl)ethyl, 3-(2-nitrophenyl)propyl, 4-(3-nitrophenyl)butyl, 1,1-dimethyl-2-(4-nitrophenyl)ethyl, -(5-nitrophenyl)pentyl, 6-(6-nitrophenyl)hexyl, 3,4-dinitrobenzyl, 2,5-dinitrobenzyl, 2,4,6-trinitrobenzyl, 2-fluoro-3-methylbenzyl, 2-chloro-4-methoxybenzyl, 1-phenyl-1-hydroxymethyl, 2-hydroxy-2-phenylethyl, 3-hydroxy-3-phenylpropyl, 4-hydroxy-4-phenylbutyl, 1,1-dimethyl-2-hydroxy-2-phenylethyl, 5-hydroxy-5-phenylpentyl, 6-hydroxy-6-phenylhexyl, 2-methyl-3-phenyl-3-hydroxypropyl, 2-(4-methoxyphenyl)-2-hydroxyethyl, 2-(3-ethoxyphenyl)-2-hydroxyethyl, 3-hydroxy-3-(4-fluorophenyl)propyl, 4-hydroxy-4-(3,4-dimethoxyphenyl)butyl, 5-hydroxy-5-(4-methylsulfinylphenyl)pentyl, 6-hydroxy-6-(2-methylphenyl)hexyl, 3-methoxybenzyl, 4-methoxybenzyl, 3-chlorobenzyl, 4-chlorobenzyl, and the like.

The phenoxy(lower)alkyl group having optionally 1 to 3 substituents selected from the group consisting of a halogen atom and a lower alkoxy group on the phenyl ring includes a phenoxyalkyl group wherein the alkyl moiety is a straight chain or branched chain alkyl group having 1 to 6 carbon atoms and the phenyl ring has optionally 1 to 3 substituents selected from the group consisting of a halogen atom and a straight chain or branched chain alkoxy group having 1 to 6 carbon atoms, for example, phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 2-methyl-3-phenoxypropyl, 2-(3-methoxyphenoxy)ethyl, 1-(4-methoxyphenoxy)ethyl, (2-methoxyphenoxy)methyl, 3-(2-ethoxyphenoxy)propyl, 4-(3-ethoxyphenoxy)butyl, 1,1-dimethyl-2-(4-ethoxyphenoxy)ethyl, 5-(4-isopropoxyphenoxy)pentyl, 6-(4-hexyloxyphenoxy)hexyl, (3,4-dimethoxyphenoxy)methyl, (3,4,5-trimethoxyphenoxy)methyl, (2,5-dimethoxyphenoxy)methyl, (2-chlorophenoxy)methyl, 2-(3-bromophenoxy)ethyl, 1-(4-chlorophenoxy)ethyl, 3-(4-fluorophenoxy)propyl, 4-(2,3-dichlorophenoxy)butyl, 1,1-dimethyl-2-(2,4-dibromophenoxy)ethyl, 5-(3,4-difluorophenoxy)pentyl, 6-(2,4,6-trichlorophenoxy)propyl, (2-chloro-6-methoxyphenoxy)methyl, and the like.

The cycloalkyl group includes a cycloalkyl group having 3 to 8 carbon atoms, for example, cyclopropyl, cyclobutyl, cyclopentyl, cyclohexyl, cycloheptyl, cyclooctyl, and the like.

The phenyl(lower)alkyl group includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, and the like.

The phenyl group having optionally 1 to 3 substituents selected from the group consisting of a halogen atom and a lower alkoxy group on the phenyl ring includes a phenyl group having optionally 1 to 3 substituents selected from the group consisting of a halogen atom and a straight chain or branched chain alkoxy group having 1 to 6 carbon atoms on the phenyl ring, for example, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methoxyphenyl, 3-methoxyphenyl, 4-methoxyphenyl, 2-ethoxyphenyl, 3-ethoxyphenyl, 4-ethoxyphenyl, 3-isopropoxyphenyl, 4-hexyloxyphenyl, 3,4-dimethoxyphenyl, 2,5-dimethoxyphenyl, 3,4,5-trimethoxyphenyl, 2-chloro-6-methoxyphenyl, 2-methoxy-3-chlorophenyl, and the like.

The phenylthio(lower)alkyl group includes a phenylthioalkyl group wherein the alkyl moiety is a straight chain or branched chain alkyl group having 1 to 6 carbon atoms, for example, phenylthiomethyl, 2-phenylthioethyl, 1-phenylthioethyl, 3-phenylthiopropyl, 4-phenylthiobutyl, 1,1-dimethyl-2-phenylthioethyl, 5-phenylthiopentyl, 6-phenylthiohexyl, 2-methyl-3-phenylthiopropyl, and the like.

The phenylsulfinyl(lower)alkyl group having optionally 1 to 3 substituents selected from the group consisting of a halogen atom and a lower alkoxy group on the phenyl ring includes a phenylsulfinylalkyl group wherein the alkyl moiety is a straight chain or branched chain alkyl group having 1 to 6 carbon atoms and the phenyl ring has 1 to 3 substituents selected from the group consisting of a halogen atom and a straight chain or branched chain alkoxy group having 1 to 6 carbon atoms, for example, phenylsulfinylmethyl, 2-phenylsulfinylethyl, 1-phenylsulfinylethyl, 3-phenylsulfinylpropyl, 4-phenylsulfinylbutyl, 1,1-dimethyl-2-phenylsulfinylethyl, 5-phenylsulfinylpentyl, 6-phenylsulfinylhexyl, 2-(3-methoxyphenylsulfinyl)ethyl, 1-(4-methoxyphenylsulfinyl)ethyl, (2-methoxyphenylsulfinyl)methyl, 3-(2-ethoxyphenylsulfinyl)propyl, 4-(3-ethoxyphenylsulfinyl)butyl, 1,1-dimethyl-2-(4-ethoxyphenylsulfinyl)ethyl, 5-(4-isopropoxyphenylsulfinyl)pentyl, 6-(4-hexyloxyphenylsulfinyl)hexyl, (3,4-dimethoxyphenylsulfinyl)methyl, (3,4,5-trimethoxyphenylsulfinyl)methyl, (2,5-dimethoxyphenylsulfinyl)methyl, (2-chlorophenylsulfinyl)methyl, 2-(3-bromophenylsulfinyl)ethyl, 1-(4-chlorophenylsulfinyl)ethyl, 3-(4-fluorophenylsulfinyl)propyl, 4-(2,3-dichlorophenylsulfinyl)butyl, 1,1-dimethyl-2-(2,4-dibromophenylsulfinyl)ethyl, 5-(3,4-difluorophenylsulfinyl)pentyl, 6-(2,4,6-trichlorophenylsulfinyl)propyl, (2-chloro-6-methoxyphenylsulfinyl)methyl, and the like.

The pyridyl(lower)alkyl group having optionally 1 to 3 substituents selected from the group consisting of a halogen atom and a lower alkoxy group on the pyridine ring includes a pyridylalkyl group wherein the alkyl moiety is a straight chain or branched chain alkyl group having 1 to 6 carbon atoms and the pyridine ring has 1 to 3 substituents selected from the group consisting of a halogen atom and a straight chain or branched chain alkoxy group having 1 to 6 carbon atoms, for example, (2-pyridyl)methyl, 2-(3-pyridyl)ethyl, 1-(4-pyridyl)ethyl, 3-(2-pyridyl)propyl, 4-(3-pyridyl)butyl, 1,1-dimethyl-2-(4-pyridyl)ethyl, 5-(2-pyridyl)pentyl, 6-(3-pyridyl)hexyl, 2-(3-methoxy-4-pyridyl)ethyl, 1-(4-methoxy-2-pyridyl)ethyl, (2-methoxy-3-pyridyl)methyl, 3-(2-ethoxy-4-pyridyl)propyl, 4-(3-ethoxy-2-pyridyl)butyl, 1,1-dimethyl-2-(4-ethoxy-3-pyridyl)ethyl, 5-(4-isopropoxy-3-pyridyl)pentyl, 6-(4-hexyloxy-2-pyridyl)hexyl, (3,4-dimethoxy-2-pyridyl)methyl, (3,4,5-trimethoxy-4-pyridyl)methyl, (2,5-dimethoxy-3-pyridyl)methyl, (2-chloro-4-pyridyl)methyl, 2-(3-bromo-2-pyridyl)ethyl, 1-(4-chloro-2-pyridyl)ethyl, 3-(4-fluoro-2-pyridyl)propyl, 4-(2,3-dichloro-4-pyridyl)butyl, 1,1-dimethyl-2-(2,4-dibromo-3-pyridyl)ethyl, 5-(3,4-difluoro-2-pyridyl)pentyl, 6-(2,4,6-trichloro-3-pyridyl)propyl, (2-chloro-6-methoxy-3-pyridyl)methyl, and the like.

The phenylsulfonyl(lower)alkyl group having optionally 1 to 3 lower alkoxy substituents on the phenyl ring includes a phenylsulfonylalkyl group wherein the alkyl moiety is a straight chain or branched chain alkyl group having 1 to 6 carbon atoms and the phenyl ring has 1 to 3 substituents of a straight chain or branched chain alkoxy group having 1 to 6 carbon atoms, for example, phenylsulfonylmethyl, 2-phenylsulfonylethyl, 1-phenylsulfonylethyl, 3-phenylsulfonylpropyl, 4-phenylsulfonylbutyl, 1,1-dimethyl-2-phenylsulfonylethyl, 5-phenylsulfonylpentyl, 6-phenylsulfonylhexyl, 2-(3-methoxyphenylsulfonyl)ethyl, 1-(4-methoxyphenylsulfonyl)ethyl, (2-methoxyphenylsulfonyl)methyl, 3-(2-ethoxyphenylsulfonyl)propyl, 4-(3-ethoxyphenylsulfonyl)butyl, 1,1-dimethyl-2-(4-ethoxyphenylsulfonyl)ethyl, 5-(4-isopropoxyphenylsulfonyl)pentyl, 6-(4-hexyloxyphenylsulfonyl)hexyl, (3,4-dimethoxyphenylsulfonyl)methyl, (3,4,5-trimethoxyphenylsulfonyl)methyl, (2,5-dimethoxyphenylsulfonyl)methyl, and the like.

The pyridyl(lower)alkyl group includes a pyridylalkyl group wherein the alkyl moiety is a straight chain or branched chain alkyl group having 1 to 6 carbon atoms, for example, (3-pyridyl)methyl, (2-pyridyl)methyl, 2-(4-pyridyl)ethyl, 1-(2-pyridyl)ethyl, 3-(2-pyridyl)propyl, 4-(2-pyridyl)ethyl, 1,1-dimethyl-2-(3-pyridyl)ethyl, 5-(2-pyridyl)pentyl, 6-(4-pyridyl)hexyl, and the like.

The benzoyl(lower)alkyl group includes a benzoylalkyl group wherein the alkyl moiety is a straight chain or branched chain alkyl group having 1 to 6 carbon atoms, for example, benzoylmethyl, 2-benzoylethyl, 1-benzoylethyl, 3-benzoylpropyl, 4-benzoylbutyl, 1,1-dimethyl-2-benzoylethyl, 5-benzoylpentyl, 6-benzoylhexyl, and the like.

The phenyl(lower)alkenyl group includes a phenylalkenyl group wherein the alkenyl moiety is a straight chain or branched chain alkenyl group having 2 to 6 carbon atoms, for example, styryl, 3-phenyl-1-propenyl, 3-phenyl-2-propenyl, 4-phenyl-3-butenyl, 4-phenyl-2-butenyl, 5-phenyl-4-pentenyl, 5-phenyl-3-pentenyl, 5-phenyl-2-pentenyl, 6-phenyl-5-hexenyl, 6-phenyl-4-hexenyl, 6-phenyl-3-hexenyl, 6-phenyl-2-hexenyl, 2-methyl-4-phenyl-3-butenyl, 2-methylstyryl, 1-methylstyryl, and the like.

The lower alkoxy(lower)alkoxy group includes an alkoxyalkoxy group wherein each alkoxy moiety is a straight chain or branched chain alkoxy group having 1 to 6 carbon atoms, for example, methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl-2-methoxyethoxy, 2-methyl-3-methoxypropoxy, and the like.

The lower alkylene group which may optionally be interrupted with an oxo group includes a straight chain or branched chain alkylene group having 1 to 6 carbon atoms which may optionally be interrupted with oxo group, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, 2-oxoethylene, 3-oxopropylene, 1-oxoethylene, 4-oxotetramethylene, 5-oxopentamethylene, 6-oxohexamethylene, and the like.

The thienyl(lower)alkyl group includes a thienylalkyl group wherein the alkyl moiety is a straight chain or branched chain alkyl group having 1 to 6 carbon atoms, for example, (2-thienyl)methyl, 2-(3-thienyl)ethyl, 1-(2-thienyl)ethyl, 3-(3-thienyl)propyl, 4-(2-thienyl)butyl, 5-(3-thienyl)pentyl, 6-(2-thienyl)hexyl, and the like.

The carbostyril derivatives of the formulae (I), (II) and (III) can be prepared by various processes, for example, by the processes shown in the following reaction schemes.

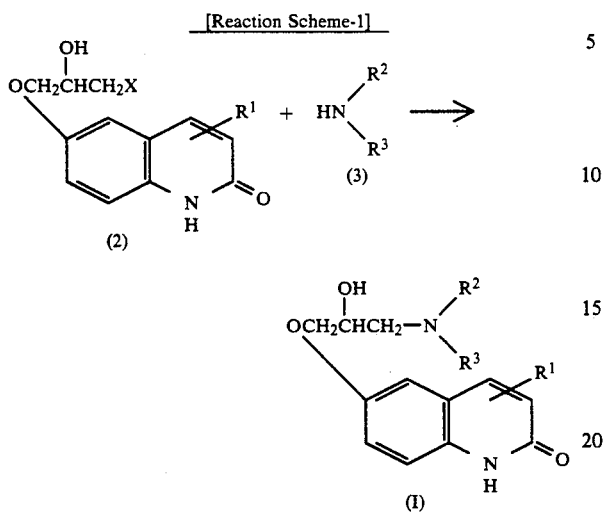

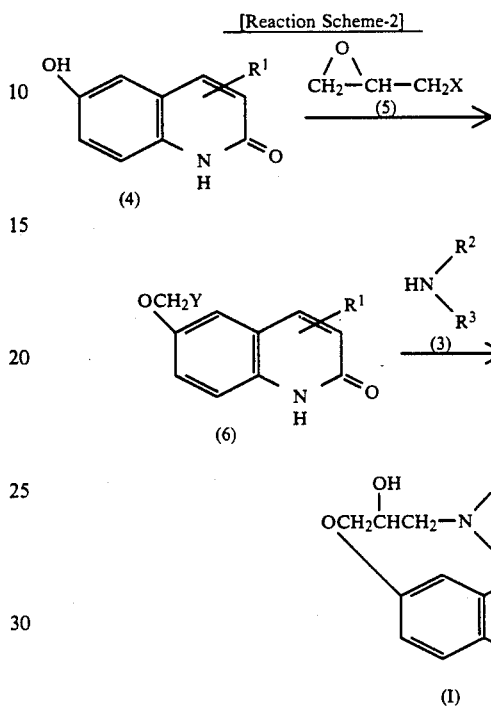

wherein $R^1$, $R^2$ and $R^3$ are the same as defined above, and X is a halogen atom, a lower alkanesulfonyloxy group, an arylsulfonyloxy group, or an aralkylsulfonyloxy group.

The reaction of the compound of the formula (2) and the compound of the formula (3) is carried out in an appropriate solvent or without solvent in the presence or absence of a basic compound. The reaction is usually carried out at a temperature of from room temperature to 200° C., preferably from room temperature to 150° C., for about 1 to 30 hours. The solvent used therein includes, for example, ethers (e.g. dioxane, tetrahydrofuran, ethylene glycol dimethyl ether, diethyl ether, etc.), aromatic hydrocarbons (e.g. benzene, toluene, xylene, etc.), lower alcohols (e.g. methanol, ethanol, isopropanol, etc.), polar solvents [e.g. dimethylformamide (DMF), dimethylsulfoxide (DMSO), hexamethylphosphoric triamide, pyridine, acetone, etc.). The basic compound include, for example, inorganic basic compounds (e.g. potassium carbonate, sodium carbonate, sodium hydroxide, potassium hydroxide, sodium hydrogen carbonate, potassium hydrogen carbonate, sodium amide, sodium hydride, potassium hydride, etc.) and organic basic compounds (e.g. triethylamine, tripropylamine, pyridine, quinoline, etc.). The above reaction proceeds advantageously by adding an alkali metal iodide (e.g. potassium iodide, sodium iodide, etc.) to the reaction system. The compound of the formula (3) is usually used at least in equimolar amount, preferably in. an amount of 1 to 5 moles to 1 mole of the compound of the formula (2).

In the above Reaction Scheme-1, the lower alkanesulfonyloxy group for X group includes, for example, methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy, and the like. The arylsulfonyloxy group includes substituted or unsubstituted arylsulfonyloxy groups, for example, phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylphenylsulfonyloxy, and the like. The aralkylsulfonyloxy group includes substituted or unsubstituted aralkylsulfonyloxy groups, for example, benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy, and the like.

wherein $R^1$, $R^2$, $R^3$ and X are the same as defined above, and Y is the group of the formula:

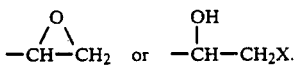

The reaction of the compound of the formula (4) and an epihalogenohydrin of the formula (5) can be carried out in the presence of a basic compound in an appropriate solvent or without solvent. The basic compound used therein includes, for example, inorganic basic compounds (e.g. sodium hydroxide, potassium hydroxide, sodium carbonate, potassium carbonate, sodium methoxide, sodium ethoxide, sodium hydride, metallic sodium, metallic potassium, sodium amide, etc.), and organic basic compounds (e.g. piperidine, pyridine, triethylamine, etc.). The solvent includes, for example, lower alcohols (e.g. methanol, ethanol, isopropanol, etc.), ketones (e.g. acetone, methyl ethyl ketone, etc.), ethers (e.g. diethyl ether, dioxane, diethylene glycol dimethyl ether, etc.), aromatic hydrocarbons (e.g. benzene, toluene, xylene, etc.), water, and the like. The compound of the formula (5) is usually used at least in equivalent amount, preferably 5 to 10 moles to 1 mole of the compound of the formula (4). The reaction is usually carried out at a temperature of from 0° to 150° C., preferably from about 50° to 100° C., for about 1 to 10 hours.

In the above reaction, the hydroxy group of the compound (4) is replaced by a (2,3-epoxy)propoxy group and 3-halogeno-2-hydroxypropoxy group by the reaction with the epihalogenohydrin of the formula (5), and thereby, the product is obtained in the form of a mixture of these substituted compounds. The mixture may be used in the subsequent reaction with the compound of the formula (3) without separation. Alternatively, the mixture may be separated into a compound having a (2,3-epoxy)propoxy group and a compound having a 3-halogeno-2-hydroxypropoxy group by a conventional separation and purification method such as recrystallization or column chromatography, and thereafter, each compound may be subjected to the reaction with the compound (3).

The reaction of the compound of the formula (6) and the compound of the formula (3) can be carried out in the presence of a basic compound in the presence or absence of a solvent. The reaction is usually carried out at a temperature of from room temperature to 200° C., preferably from about 60° to 120° C., for about 1 to 24 hours. The solvent and basic compound used therein are the same as the solvents and basic compounds as used in the reaction of the compound (2) and the compound (3) in the above Reaction Scheme-1. The compound of the formula (3) is usually used at least in equimolar amount, preferably 1 to 5 moles to 1 mole of the compound of the formula (6).

reaction system as a reaction promoter. The amount of the compound of the formula (7) is not critical, but it is usually used in an amount of 1 to 5 moles, preferably 1 to 2 moles, to 1 mole of the compound of the formula (4).

The reaction of the compound of the formula (4) and the compound of the formula (8) can be carried out under the same conditions as in the reaction of the compound (4) and the compound (5) in the above Reaction Scheme-2.

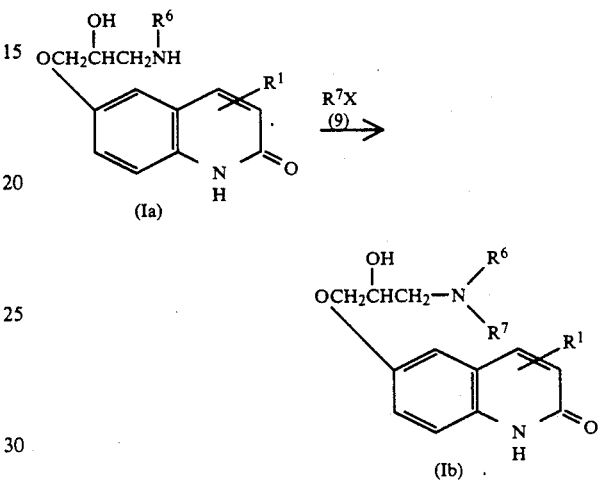

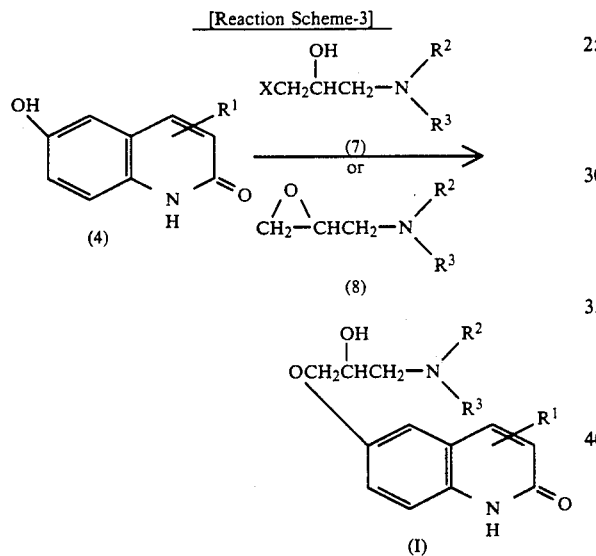

wherein $R^1$, $R^2$, $R^3$ and X are the same as defined above.

The reaction of the compound of the formula (4) and the compound of the formula (7) can be carried out in an appropriate solvent, preferably in the presence of a basic compound as a dehydrohalogenating agent and is usually carried out at a temperature of from room temperature to 200° C., preferably from 50° to 150° C., for about 1 to 15 hours. The solvent includes, for example, lower alcohols (e.g. methanol, ethanol, isopropanol, etc.), ketones (e.g. acetone, methyl ethyl ketone, etc.), ethers (e.g. diethyl ether, dioxane, diethylene glycol dimethyl ether, etc.), aromatic hydrocarbons (e.g. toluene, xylene, etc.), DMF, DMSO, hexamethylphosphoric triamide, and the like. The basic compound used as a dehydrohalogenating agent includes, for example, inorganic basic compounds (e.g. sodium hydroxide, potassium hydroxide, sodium carbonate, potassium carbonate, sodium methoxide, sodium ethoxide, potassium ethoxide, sodium hydride, metallic potassium, sodium amide, etc.), and organic basic compounds (e.g. pyridine, quinoline, triethylamine, tripropylamine, etc.). In the above reaction, an alkali metal iodide (e.g. potassium iodide, sodium iodide, etc.) may be added to the wherein $R^1$ and X are the same as defined above, and $R^6$ and $R^7$ are the same as $R^2$ and $R^3$ as defined above except that benzoyl and anilinothiocarbonyl groups are excluded.

The reaction of the compound of the formula (Ia) and the compound of the formula (9) is carried out under the same conditions as in the reaction of the compound (2) and the compound (3) in Reaction Scheme-1.

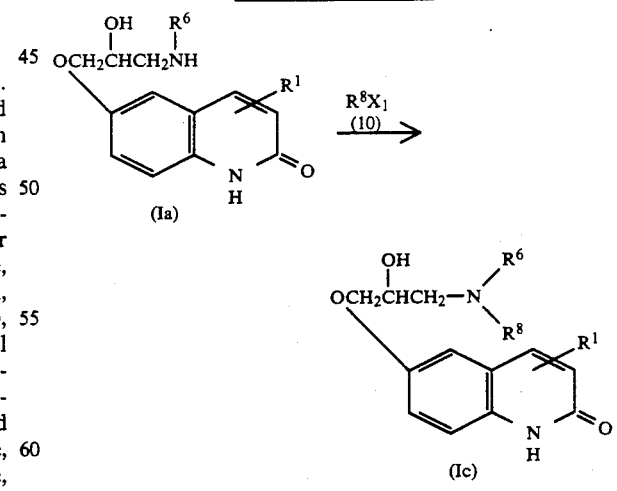

wherein $R^6$ is the same as defined above, and $R^8$ is benzoyl group and $X_1$ is hydroxy group.

The reaction of the compound of the formula (Ia) and the compound of the formula (10) can be carried out by a conventional amido bond producing reaction. The conditions for the conventional amido bond producing reaction are applicable to said reaction. The amido bond producing reaction can easily be carried out by the following various amido bond producing processes.

(a) a mixed acid anhydride process, i.e. a process of reacting the carboxylic acid compound (10) with an alkylhalocarboxylic acid to form a mixed acid anhydride and reacting the resultant with the amine compound (Ia), (b) an activated ester process, i.e. a process of converting the carboxylic acid compound (10) into an activated ester, such as p-nitrophenyl ester, N-hydroxysuccinimide ester, 1-hydroxybenzotriazole ester, etc., and reacting the resultant with the amine compound (Ia), (c) a carbodiimide process, i.e. a process of condensing the carboxylic acid compound (10) and the amine compound (Ia) in the presence of an activating agent such as dicyclohexylcarbodiimide, carbonyldiimidazole, etc., (d) other processes, i.e. a process of converting the carboxylic acid compound (10) into a carboxylic anhydride by treating it with a dehydrating agent such as acetic anhydride, and reacting the resultant with the amine compound (Ia); a process of reacting an ester of the carboxylic acid compound (10) with a lower alcohol and the amine compound (Ia) at a high temperature under high pressure; a process of reacting an acid halide compound of the carboxylic acid compound (10), i.e. a carboxylic acid halide, with the amine compound (Ia), and the like.

The mixed acid anhydride used in the above mixed acid anhydride process is obtained by the known Schotten-Baumann reaction, and the reaction product is used without isolation from the reaction mixture for the reaction with the amine compound (Ia) to give the desired compound of the formula (Ic). The Schotten-Baumann reaction is usually carried out in the presence of a basic compound. The basic compound is any conventional compound used for the Schotten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about $-20°$ to $100°$ C., preferably from about $0°$ to $50°$ C., for about 5 minutes to 10 hours, preferably about 5 minutes to 2 hours.

The reaction of the thus obtained mixed acid anhydride with the amine compound (Ia) is usually carried out at a temperature of from about $-20°$ to $150°$ C., preferably about $10°$ to $50°$ C., for about 5 minutes to 10 hours, preferably about 5 minutes to 5 hours. The mixed acid anhydride process is usually carried out in an appropriate solvent. The solvent is any conventional solvent which is usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, etc.), esters (e.g. methyl acetate, ethyl acetate, etc.), aprotic polar solvents (e.g. DMF, DMSO, hexamethylphosphoric triamide, etc.), and the like. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (10), the alkylhalocarboxylic acid and the amine (Ia) are usually used in each equimolar amount, but preferably, the alkylhalocarboxylic acid and the carboxylic acid compound (10) are used each in an amount of 1 to 1.5 mole to 1 mole of the amine (Ia).

In case of the process of reacting the carboxylic acid halide with the amine compound (Ia), the reaction is usually carried out in the presence of a basic compound in an appropriate solvent. The basic compound is any conventional compounds and includes, in addition to the basic compound used for the above-mentioned Schotten-Baumann reaction, sodium hydroxide, potassium hydroxide, sodium hydride, potassium hydride, silver carbonate, alkali metal alcoholates (e.g. sodium methylate, sodium ethylate, etc.). The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), pyridine, acetone, acetonitrile, or a mixture of these solvents. The amount of the amine compound (Ia) and the carboxylic acid halide is not critical, but the carboxylic acid halide is usually used at least in equimolar amount, preferably 1 to 5 moles to 1 mole of the amine compound (Ia). The reaction is usually carried out at a temperature of from about $-30°$ to $180°$ C., preferably from about 0 to about $150°$ C., for about 5 minutes to about 30 hours.

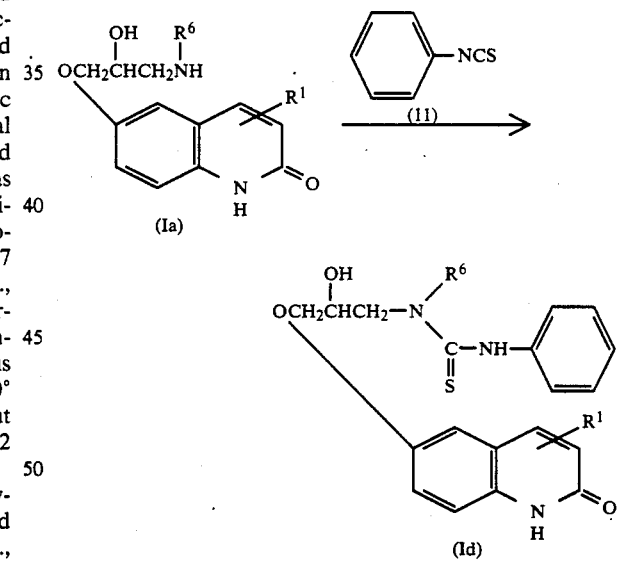

wherein $R^1$ and $R^6$ are the same as defined above.

The reaction of the compound of the formula (Ia) and a phenylisocyanate of the formula (11) can be carried out in a solvent as used in the reaction of the compound (2) and the compound (3) in Reaction Scheme-1 and is usually carried out at a temperature of from room temperature to $100°$ C., preferably from room temperature to about $70°$ C., for about 0.5 to 5 hours. The phenylisocyanate (11) is usually used in an amount of 1 to 2 moles, preferably 1 to 1.5 mole, to 1 mole of the compound of the formula (Ia).

Among the carbostyril derivatives of this invention, the compounds having a basic group can easily be converted into acid addition salts thereof by treating with a pharmaceutically acceptable acid. The acid includes, for example, inorganic acids such as hyrochloric acid, sulfuric acid, phosphoric acid, hydrobromic acid, etc., and organic acids such as oxalic acid, maleic acid, fumaric acid, malic acid, tartaric acid, citric acid, benzoic acid, acetic acid, p-toluenesulfonic acid, ethanesulfonic acid, etc.

Besides, among the carbostyril derivatives of this invention, the compounds having an acidic group can easily be converted into salts by treating with a pharmaceutically acceptable basic compound. The basic compound includes, for example, metal hydroxides such as sodium hydroxide, potassium hydroxide, calcium hydroxide, etc., alkali metal carbonates or hydrogen carbonates such as sodium carbonate, potassium hydrogen carbonate, sodium hydrogen carbonate, etc.

The compounds of this invention thus obtained can easily be isolated and purified by conventional isolation methods. The isolation methods are, for example, extraction with a solvent, dilution method, recrystallization method, column chromatography, preparative thin layer chromatography, and the like.

In addition, the compounds of this invention may be present in the form of optical isomers, and hence, this invention includes also these isomers. These isomers can easily be resoluted by conventional resolution methods, for example, by using an optical resoluting agent.

The derivatives and their salts of this invention are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspensions are sterilized and are preferably made isotonic with the blood. In the preparation of these solutions, emulsions and suspensions, there are used conventional diluents, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the compounds of the formula (I), (II) or (III), or their salts thereof of this invention (active ingredient) to be incorporated into the above pharmaceutical preparations is not specified but may be selected from a broad range, but usually, it is preferably in the range of 1 to 70% by weight, more preferably 1 to 30% by weight.

The cardiotonics of this invention may be administered in any method, and a suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the cardiotonics of this invention may be selected in accordance with the usage, ages, sexes and other conditions of the patients, the degree of severity of the diseases, and the like, but is usually in the range of about 0.1 to 10 mg of the active compound of this invention per 1 kg of body weight of the patient per day. The preparation may be administered by dividing into 2 to 4 times per day. The active compound is preferably contained in an amount of 1 to 200 mg per the dosage unit.

The present invention is illustrated by the following Reference Examples, Examples, Pharmacological test and Preparations but should not be construed to be limited thereto.

REFERENCE EXAMPLE 1

N-Methyl-N-(4-methylthiobenzyl)amine (4.2 g) and potassium carbonate (5.2 g) are dissolved in a mixture of acetone (20 ml) and water (20 ml), and thereto is added dropwise benzoy chloride (3.7 ml) gradually under ice cooling. After the mixture is stirred at the same temperature for 30 minutes, the reacting mixture is poured into water, and then extracted with dichloromethane. The extract is washed with aqueous sodium chloride solution, and dried over magnesium sulfate. Dichloromethane is distilled off to give N-benzoyl-N-methyl-N-(4-methylthiobenzyl)amine (6.8 g).

REFERENCE EXAMPLE 2

To a solution of N-benzoyl-N-methyl-N-(4-methylthiobenzyl)amine (6.8 g) in dichloromethane (120 ml) is added gradually m-chloroperoxybenzoic acid (5.5 g) with stirring at a temperature below 5° C. and the mixture is stirred at the same temperature for 15 minutes. After the reaction, the reaction mixture is washed successively with 5% aqueous potassium carbonate solution and aqueous sodium chloride solution, and subsequently dried over magnesium sulfate. After dichloromethane is distilled off from the mixture, the residue is purified by silica gel column chromatography (solvent; dichloromethane:methanol=100:0–100:5) to give N-benzoyl-N-methyl-N-(4-methylsulfinylbenzyl)amine (4.1 g).

REFERENCE EXAMPLE 3

To a mixture of ethanol (40 ml), water (20 ml) and conc. hydrochloric acid (60 ml), N-benzoyl-N-methyl-N-(4-methylsulfinylbenzyl)amine (4.1 g) is added and the mixture is heated with refluxing for 12 hours. After the reaction, the solvent is distilled off under reduced pressure, and to the resulting residue is added 20% aqueous sodium hydroxide solution, and the mixture is extracted with diethyl ether. The extract is washed successively with water and aqueous sodium chloride solution, and dried over magnesium sulfate. Diethyl ether is distilled off to give N-methyl-N-(4-methylsulfinylbenzyl)amine (2.2 g).

REFERENCE EXAMPLE 4

6-Hydroxycarbostyril (3.5 g) and S-(+)-epichlorohydrine (5 g) are added to methanol (100 ml) and thereto is added triethylamine (0.5 ml). The mixture is heated with refluxing for 8 hours. After the mixture is allowed to cool, chloroform is added thereto, and the mixture is sprinkled with silica gel and subjected to the purification by silica gel column chromatography (solvent; chloroform:methanol=100:0–100:3) to give S-6-(3-chloro-2-hydroxypropoxy)carbostyril (1.13 g).

REFERENCE EXAMPLE 5

Using R-(−)-epichlorohydrin, R-6-(3-chloro-2-hydroxypropoxy)carbostyril is obtained in the same manner as in Reference Example 4.

REFERENCE EXAMPLE 6

85% Potassium hydroxide (0.65 g) is dissolved in methanol (30 ml) and R-6-(3-chloro-2-hydroxypropoxy)carbostyril (1.03 g) is added thereto at room temperature and the mixture is stirred at the same temperature for 5 hours. After the reaction, the mixture is cooled with ice, neutralized with 1N hydrochloric acid, and then concentrated under reduced pressure at room temperature. Water is added to the residue, and the resulting crystals are collected by filtration. The crystals thus obtained are heated in methanol (15 ml) for 2–3 minutes and allowed to cool to give S-6 (2,3-epoxypropoxy)carbostyril (0.5 g).

REFERENCE EXAMPLE 7

Using S-6-(3-chloro-2-hydroxypropoxy)carbostyril, R-6-(2,3-epoxypropoxy)carbostyril is obtained in the same manner as in Reference Example 6.

EXAMPLE 1

A suspension of 6-(2,3-epoxypropoxy)carbostyril (15 g) and N-methylbenzylamine (11 g) in methanol (150 ml) is heated with refluxing for 2.5 hours. From the mixture, methanol is distilled off under reduced pressure, and to the resulting residue is added diethylether and the precipitated crystals are collected by filtration. The crystals thus obtained are purified by silica gel column chromatography (solvent; methanol:chloroform=1:100–1:25), and recrystallized from ethanol to give 6-[3-(N-methyl-N-benzylamino)-2-hydroxypropoxy]carbostyril (7.6 g), as white powder, m.p. 129°–132° C.

EXAMPLE 2

A solution of 6-(3-chloro-2-hydroxypropoxy)carbostyril (5.05 g) and N-methylbenzylamine (6.0 g) in dimethylformamide (50 ml) is heated with stirring at 50°–60° C. for 5 hours. The solvent is distilled off under reduced pressure and the resulting residue is purified by silica gel column chromatography (solvent; methanol:chloroform=1:100–1:25) and recrystallized from ethanol to give 6-[3-(N-methyl-N-benzylamino)-2-hydroxypropoxy]carbostyril (2.5 g), as white powder, m.p. 129°–132° C.

EXAMPLE 3

To a solution of 6-hydroxycarbostyril (1.6 g) and sodium hydride (50% oily) (1 g) in dimethylformamide (30 ml), 1-chloro-2-hydroxy-3-(N-methyl-N-benzylamino)propane (2.2 g) is added dropwise at room temperature. After the addition, the mixture is heated with stirring at 70°–80° C. for 3 hours. The reaction mixture is poured into water and extracted with chloroform, and the extract is dried over magnesium sulfate. Chloroform is distilled off and the resulting residue is purified by silica gel column chromatography (solvent; methanol:chloroform=1:100–1:25) and recrystallized from ethanol to give 6-[3-(N-methyl-N-benzylamino)-2-hydroxypropoxy]carbostyril (0.76 g), as white powder, m.p. 129°–132° C.

EXAMPLE 4

To a solution of N-methylbenzylamine (21 g) in methanol (50 ml), a solution of 6-(2,3-epoxypropoxy)carbostyril (4.4 g) in methanol (70 ml) is added dropwise over a period of 30 minutes under refluxing with heat. After the addition, the mixture is further heated with refluxing for 2 hours. The reaction mixture is concentrated under reduced pressure, and the resulting residue is purified by silica gel column chromatography (solvent; methanol:chloroform=1:100–1:25) and recrystallized from ethanol to give 6-[3-(N-methyl-N-benzylamino)-2-hydroxypropoxy]carbostyril (5 g), as white powder, m.p. 129°–132° C.

EXAMPLE 5

A suspension of S-(2,3-epoxypropoxy)carbostyril (15 g) and N-methyl-N-benzylamine (11 g) in methanol (150 ml) is heated with refluxing for 2 hours. Methanol is distilled off and to the resulting residue is added diethyl ether and the precipitated crystals are collected by filtration. The crystals thus obtained are purified by silica gel column chromatography (solvent; methanol:chloroform=1:100–1:25) and recrystallized 2 times from ethanol to give S-(−)-6-[3-(N-methyl-N-benzylamino)-2-hydroxypropoxy]carbostyril (9.3 g), as colorless prisms, m.p. 142°-144° C.

[α]$_D$= −32.20° (C=1.0, chloroform)

EXAMPLE 6

Using R-6-(2,3-epoxypropoxy)carbostyril as a starting material, R-(+)-6-[3-(N-methyl-N-benzylamino)-2-hydroxypropoxy]carbostyril is obtained in the same manner as in Example 5, as colorless prisms, m.p. 142°-144° C.

[α]$_D$= +31.44° (C=1.1, chloroform)

Using appropriate starting materials, the compounds of the following Table 1 are obtained in the same manners as Examples 1-4.

TABLE 1

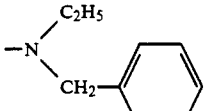

| Ex. No. | R | $R_1$ | m.p. (°C.) | Salt | Crystal. form (solvent for re-crystal.) |
|---|---|---|---|---|---|
| 7 | −N(C$_2$H$_5$)(CH$_2$C$_6$H$_5$) | H | 135-137 | Free | Colorless prisms (Ethanol) |
| 8 | −N(C$_3$H$_7$)(CH$_2$C$_6$H$_5$) | H | 135-137 | Free | White powder (Ethanol) |
| 9 | −N(C$_4$H$_9$)(CH$_2$C$_6$H$_5$) | H | 140-142 | Free | White powder (Ethanol) |
| 10 | −N(C$_5$H$_{11}$)(CH$_2$C$_6$H$_5$) | H | 129-130 | Free | Colorless needles (Methanol/water) |
| 11 | −N(CH$_2$CH$_2$OH)(CH$_2$C$_6$H$_5$) | H | 97-100 | Free | White powder (Ethyl acetate) |
| 12 | −N(CH$_2$CH=CH$_2$)(CH$_2$C$_6$H$_5$) | H | 124-125 | Free | Colorless needles (Ethanol/water) |
| 13 | −N(CH(CH$_3$)$_2$)(CH$_2$C$_6$H$_5$) | H | 148-150 | Free | White powder (Ethanol) |

TABLE 1-continued

[Structure: 6-(OCH₂CH(OH)CH₂R)-3-R¹-quinolin-2(1H)-one]

| Ex. No. | R | R₁ | m.p. (°C.) | Salt | Crystal. form (solvent for re-crystal.) |
|---|---|---|---|---|---|
| 14 | —N(CH₂CH(CH₃)₂)(CH₂C₆H₅) | H | 165–166 | Free | Colorless prisms (Ethanol) |
| 15 | —N(C₆H₅)(CH₂C₆H₅) | H | 179–181 | Free | White powder (Ethanol/chloroform) |
| 16 | —N(CH₂C₆H₅)₂ | H | 198–200 | Free | Colorless prisms (Methanol/chloroform) |
| 17 | —N(CH₃)(CH₂-C₆H₄-4-F) | H | 141–143 | Free | White powder (Ethanol) |
| 18 | —N(C₂H₅)(CH₂-C₆H₄-4-F) | H | 123–125 | Free | Colorless prisms (Ethyl acetate) |
| 19 | —N(C₃H₇)(CH₂-C₆H₄-4-F) | H | 139–140 | Free | Colorless prisms (Ethyl acetate) |
| 20 | —N(C₄H₉)(CH₂-C₆H₄-4-F) | H | 123–125 | Free | Colorless needles (Ethyl acetate/n-hexane) |
| 21 | —N(CH₃)(CH₂-C₆H₄-3-F) | H | 127–130 | Free | White powder (Ethanol) |

TABLE 1-continued

Structure: 6-(OCH₂CH(OH)CH₂R)-substituted quinolin-2(1H)-one with R¹ at position 3

| Ex. No. | R | R₁ | m.p. (°C.) | Salt | Crystal. form (solvent for re-crystal.) |
|---|---|---|---|---|---|
| 22 | -N(CH₃)-CH₂-(2-F-C₆H₄) | H | 149-150 | Free | Colorless prisms (Ethanol) |
| 23 | -N(CH₃)-CH₂-(2-OCH₃-C₆H₄) | H | 149-150 | Free | Colorless prisms (Ethanol) |
| 24 | -N(CH₃)-CH₂-(3-OCH₃-C₆H₄) | H | 134-136 | Free | Colorless prisms (Ethanol) |
| 25 | -N(C₂H₅)-CH₂-(3-OCH₃-C₆H₄) | H | 122-124 | Free | White powder (Ethyl acetate) |
| 26 | -N(C₂H₅)-CH₂-(4-OCH₃-C₆H₄) | H | 119-121 | Free | Colorless prisms (Ethanol) |
| 27 | -N(CH₃)-CH₂-(4-Cl-C₆H₄) | H | 174-176 | Free | Colorless prisms (Ethanol/chloroform) |
| 28 | -N(CH₃)-CH₂-(2-Cl-C₆H₄) | H | 155-157 | Free | Colorless prisms (Ethanol) |
| 29 | -N(CH₃)-CH₂-(4-CH₃-C₆H₄) | H | 181-183 | Free | Colorless prisms (Chloroform/methanol) |
| 30 | -N(CH₃)-C₆H₅ | H | 157-159 | Free | White powder (Ethanol) |

TABLE 1-continued

Structure:
$$\text{OCH}_2\text{CH(OH)CH}_2\text{R} - \text{[6-position of quinolin-2(1H)-one]}, \text{R}^1 \text{ at 3-position}$$

| Ex. No. | R | $R_1$ | m.p. (°C.) | Salt | Crystal. form (solvent for re-crystal.) |
|---|---|---|---|---|---|
| 31 | −N(C₂H₅)(C₆H₅) | H | 153–154 | Free | Colorless prisms (Ethanol) |
| 32 | −N(CH₃)CH₂−C₆H₄−CN (4-) | H | 145–148 | ¼ H₂O | White powder (Ethanol) |
| 33 | −N(CH₃)CH₂−C₆H₄−SCH₃ (4-) | H | 149–150 | Free | White powder (Methanol/chloroform) |
| 34 | −N(CH₃)CH₂−C₆H₄−S(=O)CH₃ (4-) | H | 153–154 | Free | White powder (Ethanol/n-hexane) |
| 35 | −N(CH₃)CH₂−C₆H₃(OCH₃)₂ (3,4-) | H | 149–151 | ½ maleate (COOH−CH=CH−COOH) | White powder (Ethanol/water) |
| 36 | −N(C₂H₅)CH₂−C₆H₃(OCH₃)₂ (3,4-) | H | 136–138 | Free | White powder (Methanol) |
| 37 | −N(C₃H₇)CH₂−C₆H₃(OCH₃)₂ (3,4-) | H | 137–139 | Free | Colorless prisms (Ethanol) |
| 38 | −N(CH₃)CH₂−C₆H₂(OCH₃)₃ (3,4,5-) | H | 162–164 | Free | White powder (Methanol) |
| 39 | −N(C₂H₅)(CH₂)₂−C₆H₅ | H | 88–90 | Free | White powder (Ethyl acetate) |

TABLE 1-continued

[Structure: quinolin-2(1H)-one with OCH₂CH(OH)CH₂R at 6-position and R¹ at 4-position]

| Ex. No. | R | R₁ | m.p. (°C.) | Salt | Crystal. form (solvent for re-crystal.) |
|---|---|---|---|---|---|
| 40 | —N(C₂H₅)(CH₂)₂O-C₆H₅ | H | 114–116 | Free | Colorless prisms (Ethyl acetate) |
| 41 | —N(C₂H₅)(CH₂)₂-C₆H₄-OCH₃ | H | 133–135 | ¼ H₂O | White powder (Ethyl acetate) |
| 42 | —N((CH₂)₂OH)((CH₂)₂-C₆H₃(OCH₃)₂) | H | 97–100 | Free | White powder (Ethyl acetate) |
| 43 | —N(C₂H₅)((CH₂)₂-C₆H₃(OCH₃)₂) | H | 100–103 | Free | White powder (Ethyl acetate) |
| 44 | —N(CH₃)(CH₂-C₆H₅) | CN (*) | 122–126 | Free | Yellow powder (Ethanol/water) |
| 45 | —N(CH₃)(CH₂C(O)N(CH₃)-C₆H₄-F) | H | 144–145 | Free | White powder (Ethyl acetate) |
| 46 | —N(CH₃)((CH₂)₂N(CH₃)-C₆H₄-F) | H | 149–151 | Free | Colorless prisms (Ethanol) |
| 47 | —N(H)(C₂H₅) | H | 188–191 | HCl | White powder (Ethanol/water) |
| 48 | —N(C₂H₅)₂ | H | 217–219 | HCl | Colorless prisms (Ethanol) |

TABLE 1-continued

Structure: 6-(OCH$_2$CH(OH)CH$_2$R)-3-R$^1$-quinolin-2(1H)-one

| Ex. No. | R | R$_1$ | m.p. (°C.) | Salt | Crystal. form (solvent for re-crystal.) |
|---|---|---|---|---|---|
| 49 | −N(H)−CH$_2$−C$_6$H$_5$ | H | 155–157 | 5/4 H$_2$O | Colorless needles (Ethanol) |
| 50 | −N(C$_2$H$_5$)−(CH$_2$)$_2$−(2-pyridyl) | H | 95–97 | Free | White powder (Ethyl acetate) |
| 51 | −N(C$_2$H$_5$)−(CH$_2$)$_3$−C$_6$H$_5$ | H | 102–104 | (COOH)$_2$ | White powder (Ethanol) |
| 52 | −N(H)−(CH$_2$)$_2$−C$_6$H$_5$ | H | 147–149 | Free | Colorless scales (Ethanol) |
| 53 | −N(H)−CH$_2$−(3-OCH$_3$-C$_6$H$_4$) | H | 138–140 | Free | White powder (Ethanol) |
| 54 | −N(CH$_2$−C$_6$H$_5$)−(CH$_2$)$_2$−(3,4-di-OCH$_3$-C$_6$H$_3$) | H | 116–119 | Free | White powder (Ethanol) |
| 55 | −N(H)−(CH$_2$)$_2$−(3,4-di-OCH$_3$-C$_6$H$_3$) | H | 190–191 | HCl | White powder (Ethanol) |
| 56 | −N(C$_2$H$_5$)−C(=O)−C$_6$H$_5$ | H | 140–143 | Free | Colorless prisms (Ethyl acetate/ ethanol) |
| 57 | −N(C$_2$H$_5$)−CH$_2$CH=CH−C$_6$H$_5$ | H | 110.5–112.5 | Free | White powder (Ethyl acetate/ n-hexane) |

TABLE 1-continued

[Structure: quinolin-2(1H)-one with OCH₂CH(OH)CH₂R substituent and R¹ substituent]

| Ex. No. | R | R₁ | m.p. (°C.) | Salt | Cryst. form (solvent for re-crystal.) |
|---|---|---|---|---|---|
| 58 | −N(C₂H₅)(CH(CH₃)(C₆H₅)) | H | 173.0–178.5 (dec.) | Free NMR[1] | Colorless prisms (Ethanol) |
| 59 | −N(C₂H₅)(CH(C₆H₅)₂) | H | 171.5–172.5 | Free | Colorless prisms (Ethyl acetate) |
| 60 | −NH−CH(CH₃)₂ | H | 170–173 | Free | Colorless prisms (Ethanol) |
| 61 | −NH−(CH₂)₃−C₆H₅ | H | 162–164 | Free | Colorless prisms (Ethanol/methanol) |
| 62 | −N(C₂H₅)((CH₂)₃S−C₆H₅) | H | 190.0–191.0 | ½ COOH-CH=CH-HOOC | Colorless needles (Ethanol/water) |
| 63 | −N(C₂H₅)((CH₂)₂O−C₆H₄−OCH₃) | H | 152.0–155.0 | ½ COOH-CH=CH-HOOC | White powder (Ethanol/water) |
| 64 | −NH−CH₃ | H | 177.5–178.5 | Free | Colorless needles (Methanol/chloroform) |
| 65 | −NH−CH(CH₃)(C₆H₅) | H | 143.5–146.5 | Free | White powder (Ethyl acetate/methanol) |

TABLE 1-continued

[Structure: 6-(OCH₂CH(OH)CH₂R)-4-(R¹)-quinolin-2(1H)-one]

| Ex. No. | R | R₁ | m.p. (°C.) | Salt | Crystal. form (solvent for re-crystal.) |
|---|---|---|---|---|---|
| 66 | −NH−CH₂CH(C₆H₅)₂ | H | 167.5–170.0 | Free | White powder (Ethyl acetate/ethanol) |
| 67 | −NH−C(CH₃)₂CH₂−C₆H₅ | H | 137.5–140.0 | Free | White powder (Ethyl acetate/ethanol) |
| 68 | −NH−CH₂−(4-Cl-C₆H₄) | H | 178.5–179.5 | Free | Colorless needles (Chloroform/methanol) |
| 69 | −NH−CH₂−(2-Cl-C₆H₄) | H | 130.0–131.0 | Free | Colorless needles (Chloroform/methanol) |
| 70 | −N(CH₃)−CH₂−(3-pyridyl) | H | 160–162 | Free | White powder (Ethanol) |
| 71 | −N(CH₃)−CH₂−(2-pyridyl) | H | 129–131 | Free | White powder (Ethanol/water) |
| 72 | −N(CH₃)−CH₂−(4-pyridyl) | H | 135–138 | Free | White powder (Ethanol/ethyl acetate) |
| 73 | −N(CH₃)−(CH₂)₂−N(CH₃)−C₆H₅ | H | 129–132 | (COOH)₂ | White powder (Ethanol/water) |

TABLE 1-continued

Structure: 6-(OCH₂CH(OH)CH₂R)-3-R¹-quinolin-2(1H)-one

| Ex. No. | R | R₁ | m.p. (°C.) | Salt | Crystal. form (solvent for re-crystal.) |
|---|---|---|---|---|---|
| 74 | -NH-CH₂-(2-methoxyphenyl) | H | 180–182 | Free | Colorless needles (Chloroform/methanol) |
| 75 | -NH-CH(phenyl)₂ | H | 180–182 | Free | Colorless prisms (Ethanol) |
| 76 | -NH-CH₂-(4-methoxyphenyl) | H | 190–192 | Free | Colorless needles (Methanol) |
| 77 | -NH-CH₂-(3-fluorophenyl) | H | 146.5–147.5 | Free | White powder (Ethanol) |
| 78 | -N(CH₃)-(CH₂)₂S-phenyl | H | 138.0–140.0 | Free | White powder (Chloroform/methanol) |
| 79 | -NH-CH₂-(4-fluorophenyl) | H | 182.5–184.0 | Free | Colorless needles (Methanol/chloroform) |
| 80 | -N(CH₂-phenyl)(CH₂)O-(3-methoxyphenyl) | H | 124.0–125.5 | Free | Colorless prisms (Ethanol) |
| 81 | -N(CH₃)-C(=S)-NH-phenyl | H | 185.0–186.5 (dec.) | Free | White powder (Chloroform/methanol) |

TABLE 1-continued

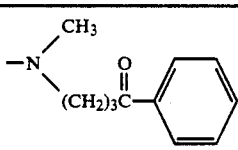

| Ex. No. | R | R₁ | m.p. (°C.) | Salt | Crystal. form (solvent for re-crystal.) |
|---|---|---|---|---|---|
| 82 | 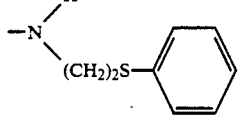 | H | 126.0–128.5 | Free | Colorless prisms (Ethanol/water) |
| 83 | 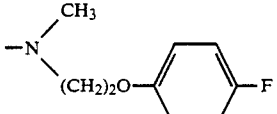 | H | 152.5–153.5 | Free | White powder (Chloroform/methanol) |
| 84 | 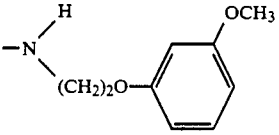 | H | 174.0–176.5 | Free | Colorless prisms (Dimethyl-formamide/ethanol) |
| 85 | 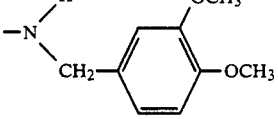 | H | 186.0–187.0 | HCl | Colorless prisms (Ethanol/water) |
| 86 | 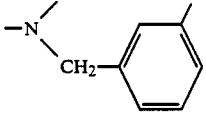 | H | 156.0–157.0 | Free | White powder (Methanol) |
| 87 | 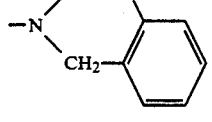 | H | 138.0–139.0 | Free | Colorless needles (Methanol) |
| 88 | 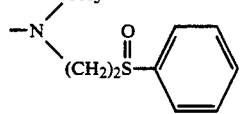 | H | 174.5–175.5 | Free | Colorless needles (Methanol) |
| 89 | 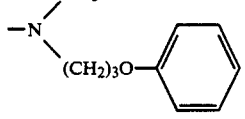 | H | 84–86 | Free | Colorless needles (Diethylether/dichloromethane) |
| 90 | | H | 127.5–130.0 | Free | Colorless prisms (Ethyl acetate) |

TABLE 1-continued

Structure: 6-(OCH₂CH(OH)CH₂R)-3-R¹-quinolin-2(1H)-one

| Ex. No. | R | R₁ | m.p. (°C.) | Salt | Crystal. form (solvent for re-crystal.) |
|---|---|---|---|---|---|
| 91 | −N(CH₃)(CH₂)₃CH(OH)C₆H₅ | H | 60–63 | Free | Colorless needles (n-Hexane/ethyl acetate) |
| 92 | −N(CH₂C₆H₅)(CH₂)₂-(2-OCH₃-C₆H₄) | H | 156.5–158.5 | Free | Colorless scales (Methanol) |
| 93 | −N(CH₂-C₆H₅)(CH₂)₂-(4-OCH₃-C₆H₄) | H | 130.0–132.0 | Free | Colorless prisms (Ethanol/water) |
| 94 | −N(C₂H₅)(CH₂-(4-SCH₃-C₆H₄)) | H | 113–115 | Free | Colorless prisms (Ethanol) |
| 95 | −N(CH₂CH₂OH)(CH₂)₂-(3-OCH₃-C₆H₄) | H | 98–100 | Free | Colorless needles (Ethanol/ethyl acetate) |
| 96 | −N(cyclopropyl)(CH₂-C₆H₅) | H | 168–170 | Free | Colorless prisms (Chloroform/methanol) |
| 97 | −N(CH₂-C₆H₅)(CH₂)₂N(CH₃)C₆H₅ | H | 150–151 | Free | Colorless needles (Chloroform/methanol) |
| 98 | −N(H)(CH₂)₂N(CH₃)C₆H₅ | H | 135–136 | Free | White powder (Ethanol) |

TABLE 1-continued

Structure: 6-(OCH₂CH(OH)CH₂R)-quinolin-2(1H)-one with R¹ at position 3

| Ex. No. | R | R₁ | m.p. (°C.) | Salt | Crystal. form (solvent for re-crystal.) |
|---|---|---|---|---|---|
| 99 | −N((CH₂)₂OH)(CH₂−C₆H₄−4-F) | H | 116–118 | Free | Colorless prisms (Ethyl acetate) |
| 100 | −NH−CH₂−C₆H₄−3-OC₂H₅ | H | 195–197 | HCl | White powder (Ethanol/water) |
| 101 | −N(CH₂−C₆H₄−4-OCH₃)(CH₂CH₂−C₆H₅) | H | 163.0–165.0 | Free | Colorless prisms (Methanol/chloroform) |
| 102 | −NH−(CH₂)₂−C₆H₄−3-OCH₃ | H | 204.5–206.5 | HCl | Colorless needles (Ethanol) |
| 103 | −NH−(CH₂)₂−C₆H₄−4-OCH₃ | H | 248.0–250.0 | HCl | Colorless prisms (Ethanol/water) |
| 104 | −NH−(CH₂)₂−C₆H₄−2-OCH₃ | H | 206.5–208.5 | HCl | Colorless prisms (Ethanol) |
| 105 | −NH−(CH₂)₃S−C₆H₅ | H | 117.0–119.0 | Free | Colorless needles (Methanol) |
| 106 | −N((CH₂)₂OH)(CH₂−C₆H₄−3-OCH₃) | H | 76–78 | Free | Yellow powder (Ethyl acetate) |
| 107 | −NH−CH₂−C₆H₄−4-CH₃ | H | 167.5–169 | Free | White powder (Methanol) |

TABLE 1-continued

Structure: 3,4-dihydrocarbostyril with OCH₂CH(OH)CH₂R substituent and R¹ substituent

| Ex. No. | R | R₁ | m.p. (°C.) | Salt | Crystal. form (solvent for re-crystal.) |
|---|---|---|---|---|---|
| 108 | −N(H)−CH₂−C₆H₄−4-NO₂ | H | 177–178.5 | Free | Yellow needles (Methanol) |
| 109 | −N(H)−(CH₂)₂−C₆H₄−4-F | H | 176–178 | Free | White powder (Methanol) |
| 110 | −N(H)−(CH₂)₂−C₆H₄−4-Cl | H | 181–182.5 | Free | White powder (Methanol) |
| 111 | −N(H)−CH₂−C₆H₄−4-CN | H | 191–193 | Free | White powder (Methanol/chloroform) |
| 112 | −N(H)−CH₂−(2-pyridyl) | H | 142–144 | Free | White powder (Ethanol) |
| 113 | −N(C₂H₅)−(CH₂)₂−C₆H₄−3-OCH₃ | H | 170.0–171.5 | HOOC−CH=CH−COOH | Colorless prisms (Ethanol) |
| 114 | −N(H)−CH₂−C₆H₄−3-OCH₂OCH₃ | H | 153–154.5 | Free | White powder (Methanol/diethylether) |
| 115 | −N(CH₃)−CH₂CH(OH)−C₆H₅ | H | 133.0–136.0 | Free | Colorless needles (Ethyl acetate) |
| 116 | −N(CH₂−C₆H₅)(CH₂CH(OH)−C₆H₅) | H | 183.5–185.5 | Free | Colorless needles (Ethyl acetate/ethanol) |

TABLE 1-continued
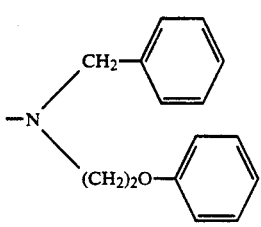
| Ex. No. | R | $R_1$ | m.p. (°C.) | Salt | Crystal form (solvent for re-crystal.) |
|---|---|---|---|---|---|
| 117 | 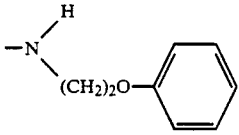 | H | 127.5–128.5 | Free | Colorless needles (Ethyl acetate) |
| 118 | 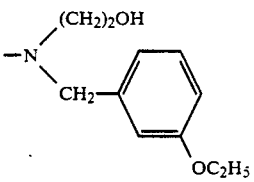 | H | 232.5–234.0 | HCl | Colorless prisms (Ethanol/water) |
| 119 | 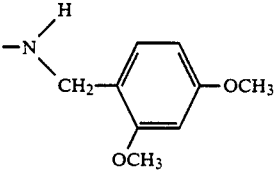 | H | 93–95 | Free | White powder (Ethyl acetate) |
| 120 | 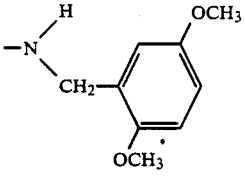 | H | 228–230 | HCl | White powder (Ethanol/water) |
| 121 | 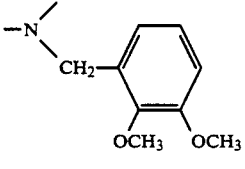 | H | 171.0–172.0 | Free | Colorless needles (Methanol) |
| 122 | 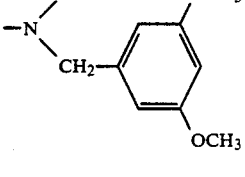 | H | 184.5–186.0 | Free | Colorless needles (Methanol) |
| 123 |  | H | 111–113 (dec.) | HCl | White powder (Ethanol/water) |

TABLE 1-continued

Structure: 6-(OCH₂CH(OH)CH₂R)-3-R¹-carbostyril (2-oxo-1H-quinoline)

| Ex. No. | R | R₁ | m.p. (°C.) | Salt | Crystal. form (solvent for re-crystal.) |
|---|---|---|---|---|---|
| 124 | −N(CH₃)−(CH₂)₂S(O)−C₆H₄−F | H | 126–129 | Free | White powder (Dichloromethane/ diethylether) |
| 125 | −N(CH₃)−(CH₂)₃N(CH₃)−C₆H₅ | H | 103.5–105.5 | Free | Colorless prisms (Ethyl acetate/ n-hexane) |
| 126 | −N(CH₃)−(CH₂)₂C(O)−N(CH₃)−C₆H₅ | H | 138.5–139.5 | Free | Colorless prisms (Ethyl acetate/ ethanol) |
| 127 | −N(H)−CH₂−C₆H₂(OCH₃)₃ (3,4,5-trimethoxy) | H | 145–148 (dec.) | HCl | White powder (Ethanol/ water) |
| 128 | −N(H)−CH₂−C₆H₄−S(O)CH₃ | H | 123–125 (dec.) | Free | White powder (Ethanol) |
| 129 | −N(CH₃)−(CH₂)₂S(O)₂−C₆H₅ | H | 154.0–155.0 | Free | Colorless scales (Methanol) |
| 130 | −N(CH₃)−(CH₂)₂S(O)₂−C₆H₄−OCH₃ | H | 155.0–156.5 | Free | Colorless prisms (Methanol) |
| 131 | −N(CH₃)−(CH₂)₂S(O)−C₆H₄−OCH₃ | H | 99.0–102.0 | (COOH)₂· 2H₂O | White powder (Ethanol/ water) |

(*); 3-position of carbostyril nucleus
NMR[1]: 200MHz(CDCl₃)δppm;
1.09(3H, t, J=7.2Hz), 1.36–1.46(3H, m), 2.42–2.85(4H, m), 3.70(1H, broads), 3.90–4.05(4H, m), 6.71(1H, d, J=9.4Hz), 6.95(1H, d, J=2.4Hz), 7.14(1H, dd, J=9.0Hz, 2.4Hz), 7.25–7.37(6H, m), 7.72(1H, d, J=9.4Hz), 11.83(1H, broads)

EXAMPLE 132

A suspension (50 ml) of 6-(3-methylamino-2-hydroxypropoxy)carbostyril (3.0 g), sodium iodide (11.8 g), triethylamine (2.2 ml) and 2-(4-fluorophenylsulfinyl)ethyl bromide (3.9 g) in dimethylformamide is heated with stirring at 80°–90° C. for 5 hours. After concentration under reduced pressure, the resulting residue is purified by silica gel column chromatography (solvent; dichloromethane:methanol:ammonium hydroxide=200:10:1–150:10:1) and recrystallized from dichloromethane-diethylether to give 6-[3-{N-[2-(4-fluorophenylsulfinyl)ethyl]-N-methylamino)-2-hydroxypropoxy]carbostyril (0.7 g), as white powder, m.p. 126°–129° C.

Using appropriate starting materials, the compounds of the above Examples 7–80, 82–123, and 125–131 are obtained in the same manner as Example 132.

EXAMPLE 133

To a suspension of 6-(3-methylamino-2-hydroxypropoxy)carbostyril (0.7 g) in ethanol (10 ml) is added phenylisothiocyanate (0.35 ml) at room temperature, and the mixture is stirred at the same temperature for 1 hour. The insoluble product is collected by filtration and recrystallized from chloroform-methanol to give 6-[3-(1-methyl-3-phenylthioureido)-2-hydroxypropoxy]carbostyril (0.83 g), as white powder, m.p. 185.0°–186.5° C. (decomp.).

Using appropriate starting materials, the compounds of the following Table 2 are obtained in the same manners as Examples 1–4, and 132.

TABLE 2

| Ex. No. | R | m.p. (°C.) | Salt | Crystal. form (solvent for re-crystal.) |
|---|---|---|---|---|
| 134 | –N(CH₂CH₂OH)(CH₂–C₆H₄–OC₂H₅) | 139–141 | Free | White powder (Ethanol) |
| 135 | –N(H)(CH₂–C₆H₄–OC₂H₅) | 237–239 | HCl | White powder (Ethanol/water) |
| 136 | –N(CH₃)((CH₂)₃–S–C₆H₅) | 84–86 | Free | White powder (Isopropanol) |
| 137 | –N(CH₃)((CH₂)₃–S(=O)–C₆H₅) | 141–146 | ½ COOH–CH=CH–COOH | White powder (Ethanol) |
| 138 | –N(CH₃)((CH₂)₂–S(=O)–C₆H₅) | 158–161 | ½ COOH–CH=CH–COOH | Colorless powder (Ethanol) |
| 139 | –N(H)(CH₂–C₆H₃(OCH₃)₂) | 215–218 | HCl. 1.5 H₂O | White powder (Ethanol/water) |
| 140 | –N(CH₃)(cyclohexyl) | 124–126 | Free | White powder (Ethanol/water) |

TABLE 2-continued

Structure: 6-(OCH₂CH(OH)CH₂R)-quinolin-2(1H)-one

| Ex. No. | R | m.p. (°C.) | Salt | Crystal. form (solvent for re-crystal.) |
|---|---|---|---|---|
| 141 | -NH-CH₂-(3-H₃CO, 5-S(=O)CH₃)phenyl | 235–238 (dec.) | HCl. ½H₂O | White powder (Ethanol/water) |
| 142 | -N(CH₃)-CH₂-(4-OCH₃)pyridin-2-yl | 108–110 | 2H₂O | White powder (Ethanol/water) |
| 143 | -N(CH₃)-CH₂-(4-Cl)pyridin-2-yl | 159–161 | Free | Colorless prisms (Ethanol/water) |
| 144 | -NH-CH₂-(4-Cl)pyridin-2-yl | 95–98 | H₂O | White powder (Ethyl acetate) |
| 145 | -NH-CH₂-(thiophen-2-yl) | NMR[2] | H₂O | White powder (Ethanol) |
| 146 | -NH-CH₂-(4-OCH₃)pyridin-2-yl | 179–181 | Free | White powder (Ethanol/water) |
| 147 | -NH-(CH₂)₂-S(=O)-phenyl | 176–179 | Free | Colorless prisms (Methanol) |
| 148 | -N(CH₂CH₂OH)-CH₂-pyridin-2-yl | 86–89 | Free | White powder (Methanol) |
| 149 | -N(CH₃)-pyridin-2-yl | 225–227 (dec.) | Free | Light yellow prisms (Methanol) |

TABLE 2-continued

Structure: 6-(OCH2CH(OH)CH2R)-quinolin-2(1H)-one

| Ex. No. | R | m.p. (°C.) | Salt | Crystal. form (solvent for re-crystal.) |
|---|---|---|---|---|
| 150 | −N(CH3)−C(=O)−CH2−N(CH3)−C6H5 | 58−69 | Free | White powder |
| 151 | −N(CH3)−C(=O)−(CH2)2−N(CH3)−C6H5 | 47−50 | Free | White powder |
| 152 | −NH−CH2−(C6H3)(S(=O)CH3)(OCH3) | 108−110 | HCl. 2.5 H2O | White powder (Ethanol/water) |
| 153 | −N(CH3)−(CH2)2−SO2−C6H4−OCH3 | 155.0−156.5 | Free | Colorless prisms (Methanol) |
| 154 | −N(CH3)−(CH2)2−S(=O)−C6H4−OCH3 | 99.0−102.0 | (COOH)2. 2H2O | White powder (Ethanol/water) |
| 155 | −NH−CH2−(C6H3)(OCH3)(OCH3) | 228−230 | HCl | White powder (Ethanol/water) |
| 156 | −NH−CH2−(C6H3)(OCH3)(OCH3) | 171.0−172.0 | Free | Colorless needles (Methanol) |
| 157 | −NH−CH2−(C6H3)(OCH3)(OCH3) | 184.5−186.0 | Free | Colorless needles (Methanol) |

TABLE 2-continued

Structure: 6-(OCH₂CH(OH)CH₂R)-substituted quinolin-2(1H)-one with R at 5-position

| Ex. No. | R | m.p. (°C.) | Salt | Crystal. form (solvent for re-crystal.) |
|---|---|---|---|---|
| 158 | -N(H)-CH₂-(3,5-dimethoxyphenyl) | 111-113 (dec.) | HCl | White powder (Ethanol/water) |
| 159 | -N(CH₃)-(CH₂)₂-S(=O)-(4-fluorophenyl) | 126-129 | Free | White powder (Methylene chloride/diethylether) |
| 160 | -N(CH₃)-(CH₂)₃-N(CH₃)-phenyl | 103.5-105.5 | Free | Colorless prisms (Ethyl acetate/n-hexane) |
| 161 | -N(CH₃)-(CH₂)₂-C(=O)-N(CH₃)-phenyl | 138.5-139.5 | Free | Colorless prisms (Ethyl acetate/ethanol) |
| 162 | -N(H)-CH₂-(3,4,5-trimethoxyphenyl) | 145-148 (dec.) | HCl | White powder (Ethanol/water) |
| 163 | -N(H)-CH₂-(4-(S(=O)CH₃)phenyl) | 123-125 (dec.) | Free | White powder (Ethanol) |
| 164 | -N(CH₃)-(CH₂)₃-S(=O)₂-phenyl | 154.0-155.0 | Free | Colorless scales (Methanol) |
| 165 | -N((CH₂)₂OH)-CH₂-(3-ethoxyphenyl) | 93-95 | Free | White powder (Ethyl acetate) |

NMR[2]: 200MHZ(DMSO-d₆)δppm; 2.50(1H, brs), 2.65(2H, m), 3.91(2H, s), 3.80–4.10(3H, m), 5.02(1H, s), 6.48(1H, d, J=9.5Hz), 6.90–7.10(2H, m), 7.10–7.30(4H, m), 7.30–7.50(1H, m), 7.83(1H, d, J=9.5Hz)

EXAMPLES 166-171

Using appropriate starting materials, the compounds of the following Table 3 are obtained in the same manner as Example 5.

TABLE 3

Structure: 6-(OCH$_2$CH(OH)CH$_2$R)-substituted quinolin-2(1H)-one (* denotes chiral center)

| Ex. No. | R | m.p. (°C) | Salt | (Optical properties)* | Crystal. form (solvent for re-crystal.) |
|---|---|---|---|---|---|
| 166 | −N(H)−CH$_2$−(3,4-dimethoxyphenyl) | 153−155 | Free | R−(+) $[\alpha]_D^{20} = +9.5°$ (c = 0.44, methanol) | Colorless needles (Methanol) |
| 167 | −N(H)−CH$_2$−(4-methoxyphenyl) | 104−106 | Free | S−(−) $[\alpha]_D^{20} = -8.7°$ (c = 1.0, methanol) | Colorless needles (Ethanol) |
| 168 | −N(H)−CH$_2$−(4-methoxyphenyl) | 107−109 | Free | R−(+) $[\alpha]_D^{20} = +9.0$ (c = 1.0, methanol) | Colorless needles (Ethanol) |
| 169 | −N(H)−CH$_2$−(3,4-dimethoxyphenyl) | 154−155 | Free | S−(−) $[\alpha]_D^{20} = -9.4°$ (c = 0.51, methanol) | Colorless needles (Methanol) |
| 170 | −N(CH$_3$)−CH$_2$−phenyl | 142−144 | Free | S−(−) $[\alpha]_D^{20} = -32.2°$ (c = 1.0, chloroform) | Colorless prisms (Ethanol) |
| 171 | −N(CH$_3$)−CH$_2$−phenyl | 142−144 | Free | R−(+) $[\alpha]_D^{20} = +31.44°$ (c = 1.1, chloroform) | Colorless prisms (Ethanol) |

EXAMPLES 172-173

Using the appropriate starting materials, the compounds of the following Table 4 are obtained in the same manner as in Examples 1-4, and 132.

TABLE 4

Structure: 6-(OCH$_2$CH(OH)CH$_2$R)-substituted quinolin-2(1H)-one

| Ex. No. | R | m.p. (°C) | Salt | Crystal. form (solvent for re-crystal.) |
|---|---|---|---|---|
| 172 | −N(H)−CH$_2$−(3,4-diethoxyphenyl) | 159−161 | HCl | White powder (Ethanol) |

TABLE 4-continued $$\text{OCH}_2\text{CHCH}_2\text{R with OH, on quinolin-2(1H)-one 6-position}$$

| Ex. No. | R | m.p. (°C.) | Salt | Crystal. form (solvent for re-crystal.) |
|---|---|---|---|---|
| 173 | -N(CH₃)(CH₂)₃SO₂C₆H₅ | 151-153 | ½ COOH-CH=CH-COOH (maleate) | Colorless prisms (Ethanol/water) |

EXAMPLES 174–186

Using appropriate starting materials, the compounds of the following Table 5 are obtained in the same manner as in Example 5.

TABLE 5

$$\text{OCH}_2\overset{*}{\text{CH}}(\text{OH})\text{CH}_2\text{R on quinolin-2(1H)-one 6-position}$$

| Ex. No. | R | m.p. (°C.) | Salt | (Optical properties) | Crystal. form (solvent for re-crystal.) |
|---|---|---|---|---|---|
| 174 | -NH-CH₂-C₆H₄-F (4-) | 130-132 | Free | R-(+) $[\alpha]_D^{20} = +9.8°$ (c = 0.55, chloroform: methanol = 1:1) | White powder (Ethanol) |
| 175 | -NH-CH₂-C₆H₄-F (4-) | 130-132 | Free | S-(-) $[\alpha]_D^{20} = -10.0°$ (c = 0.65, chloroform: methanol = 1:1) | White powder (Ethanol) |
| 176 | -NH-CH₂-C₆H₄-OCH₃ (4-) | 240-241 | HCl | R-(+) $[\alpha]_D^{20} = +4.3°$ (c = 0.79, methanol: water = 1:1) | Colorless prisms (Methanol) |
| 177 | -NH-CH₂-C₆H₄-OCH₃ (4-) | 239-240 | HCl | S-(-) $[\alpha]_D^{20} = -4.5$ (c = 0.76, methanol: water = 1:1) | Colorless prisms (Ethanol/water) |
| 178 | -NH-CH₂-C₆H₄-OC₂H₅ | 169-170 | HCl | R-(+) $[\alpha]_D^{20} = +9.5°$ (c = 0.69, methanol: water = 1:1) | White powder (Ethanol) |

TABLE 5-continued

Structure: 6-(OCH₂CH(OH)*CH₂R)-substituted quinolin-2(1H)-one

| Ex. No. | R | m.p. (°C.) | Salt | *(Optical properties) | Crystal. form (solvent for re-crystal.) |
|---|---|---|---|---|---|
| 179 | -N(H)(CH₂-C₆H₄-3-OC₂H₅) | 169-171 | HCl | S-(-) $[\alpha]_D^{20} = -9.3°$ (c = 0.69, methanol:water = 1:1) | White powder (Ethanol) |
| 180 | -N(H)(CH₂-C₆H₄-4-Cl) | 258-260 | HCl | R-(+) $[\alpha]_D^{20} = +8.1°$ (c = 0.62, methanol:water = 1:1) | Colorless prisms (Ethanol/water) |
| 181 | -N(H)(CH₂-C₆H₄-4-Cl) | 253-255 | HCl | S-(-) $[\alpha]_D^{20} = -7.9°$ (c = 0.58, methanol:water = 1:1) | Colorless prisms (Ethanol/water) |
| 182 | -N(CH₂CH₂OH)(CH₂-C₆H₄-4-F) | 109-111 | Free | R-(+) $[\alpha]_D^{20} = +4.3°$ (c = 1.54, dimethylformamide) | Colorless prisms (Ethyl acetate) |
| 183 | -N(CH₂CH₂OH)(CH₂-C₆H₄-4-F) | 107-109 | Free | S-(-) $[\alpha]_D^{20} = -4.9°$ (c = 1.67, dimethylformamide) | Colorless prisms (Ethyl acetate) |
| 184 | -N(H)(CH₂-C₆H₃-3,4-(OC₂H₅)₂) | 174-176 | HCl | R-(+) $[\alpha]_D^{20} = +2.6°$ (c = 0.62, methanol:water = 1:1) | Colorless prisms (Ethanol/water) |
| 185 | -N(H)(CH₂-C₆H₃-3,4-(OC₂H₅)₂) | 174-176 | HCl | S-(-) $[\alpha]_D^{20} = -2.4°$ (c = 0.66, methanol:water = 1:1) | Colorless prisms (Ethanol/water) |
| 186 | -N(H)(CH₂-C₆H₃-3,5-(OCH₃)₂) | 79-81 | Free | R-(+) $[\alpha]_D^{20} = +9.9°$ (c = 0.99, chloroform:methanol = 1:1) | White powder (Ethanol) |

Pharmacological test

The pharmacological activities of the compounds of the present invention were tested as follows:

Method

Female and male adult mongrel dogs, weighing 8–13 kg, were anesthetized by intravenous injection of sodium pentobarbital (30 mg/kg) After intravenous injection of sodium heparin (1,000 U/kg), the dogs were killed by bleeding and the heart was taken out The heart sample comprised mainly papillary muscle and septum of ventricles of heart, and was perfused through a canule inserted into an anteroseptal with the blood from the donor dog at a constant perfusion pressure of 100 mmHg. The donor dog, weighing 18–27 kg, was anesthetized by intravenous injection of sodium pentobarbital (30 mg/kg), and further, sodium heparin (1,000 U/kg) was administered to the donor dog by intravenous injection.

The papillary muscle was stimulated with square wave at the stimulate pulse duration of 5 msec and the frequency of 120/minute, at 1.5 times voltage (0.5–3 V) using a bipolar electrode. The papillary muscle showed a steady tension of 1.5 g. The tension produced by stimulation of the papillary muscle was measured with a power displacement transducer. The produced tension was recorded on an ink-writing oscillograph. The detailed explanation of this experimental test method is disclosed by Endo and Hashimoto (cf. Am. J. Physiol., 218, 1459–1463, 1970).

Test compounds were administered into the artery at a volume of 10 to 30 μl for 4 seconds. Regression analysis was carried out using the measurement at the doses of 10, 100, 1,000 nmole of the test compound, and $ED_{30}$ was determined from the regression equation $ED_{30}$ means the amount of the test compounds by which the contraction of the papillary muscle is increased by 30% in comparison with that of the control. Using amrinone in the control test instead of the test compound, the value of $$\frac{ED_{30} \text{ of amrinone}}{ED_{30} \text{ of test comp.}}$$

was determined, and the inotropic activity of the test compounds is shown by this value.

Results

The results are shown in the following Table 6.

Test compounds 1. 6-[3-(N-Methyl-N-benzylamino)-2-hydroxypropoxy]carbostyril
2. 6-[3-(N-Ethyl-N-benzylamino)-2-hydroxypropoxy]carbostyril
3. 6-[3-(N-Ethyl-N-β-phenethylamino)-2-hydroxypropoxy]carbostyril
4. 6-[3-(N-Propyl-N-(benzylamino)-2-hydroxypropoxy]carbostyril
5. 6-{3-[N-Methyl-N-(4-chlorobenzyl)amino]-2-hydroxy-propoxy}carbostyril
6. 6-[3-(N-Methylanilino)-2-hydroxypropoxy]carbostyril
7. 6-[3-(N-Ethylanilino)-2-hydroxypropoxy]carbostyril
8. 6-{3-[N-Methyl-N-(2-fluorobenzyl)amino]-2-hydroxypropoxy}carbostyril
9. 6-[3-(N-n-Butyl-N-benzylamino)-2-hydroxypropoxy]carbostyril
10. 6-{3-[N-Methyl-N-(2-chlorobenzyl)amino]-2-hydroxypropoxy}carbostyril
11. 6-{3-[N-Ethyl-N-(2-phenoxyethyl)amino]-2-hydroxypropoxy}carbostyril
12. 6-{3-[N-Methyl-N-(4-methylthiobenzyl)amino]-2-hydroxypropoxy}carbostyril
13. 6-[3-(N-Allyl-N-benzylamino)-2-hydroxypropoxy]carbostyril
14. 6-[3-{N-Ethyl-N-[2-(4-methoxyphenyl)ethyl]amino}-2-hydroxypropoxy]carbostyril.¼ hydrate
15. 6-{3-[N-Methyl-N-{2-[N-methyl-(4-fluoroanilino)]ethyl}amino]-2-hydroxypropoxy}carbostyril
16. 6-{3-[N-Ethyl-N-(3-methoxybenzyl)amino]-2-hydroxypropoxy}carbostyril
17. 6-{3-[N-n-Propyl-N-(3,4-dimethoxybenzyl)amino]-2-hydroxypropoxy}carbostyril
18. 6-[3-(3-Phenylpropyl)amino-2-hydroxypropoxy]carbostyril
19. 6-[3-(3-Methoxybenzyl)amino-2-hydroxypropoxy]carbostyril
20. 6-[3-{N-Benzyl-N-[2-(3,4-dimethoxyphenyl)ethyl]amino}-2-hydroxypropoxy]carbostyril
21. 6-[3-(N-Ethyl-N-benzoylamino)-2-hydroxypropoxy]carbostyril
22. 6-{3-[N-Ethyl-N-(3-phenyl-2-propenyl)amino]-2-hydroxypropoxy}carbostyril
23. 6-{3-[N-Ethyl-N-(1-phenylethyl)amino]-2-hydroxypropoxy}carbostyril
24. 6-[3-{N-Ethyl-N-[2-(3-methoxyphenyl)ethyl]amino}-2-hydroxypropoxy]carbostyril.¼ fumarate
25. 6-[3-(2,2-Diphenylethylamino)-2-hydroxypropoxy]carbostyril
26. 6-[3-(4-Chlorobenzylamino)-2-hydroxypropoxy]carbostyril
27. 6-[3-(2-Chlorobenzylamino)-2-hydroxypropoxy]carbostyril
28. 6-{3-[N-Methyl-N-(2-pyridylmethyl)amino]-2-hydroxypropoxy}carbostyril
29. 6-{3-[N-Methyl-N-[2-(N-methylanilino)ethyl]amino}-2-hydroxypropoxy]carbostyril.oxalate
30. 6-[3-(2-Methoxybenzylamino)-2-hydroxypropoxy]carbostyril
31. 6-[3-(4-Methoxybenzylamino)-2-hydroxypropoxy]carbostyril
32. 6-[3-(3-Fluorobenzylamino)-2-hydroxypropoxy]carbostyril
33. 6-[3-(2-Phenylthioethyl)amino-2-hydroxypropoxy]carbostyril
34. 6-[3-(4-Fluorobenzyl)amino-2-hydroxypropoxy]carbostyril
35. 6-[3-(1-Methyl-3-phenylthioureido)-2-hydroxypropoxy]carbostyril
36. 6-{3-[N-Methyl-N-(3-benzoylpropyl)amino]-2-hydroxypropoxy}carbostyril
37. 6-{3-[2-(3-Methoxyphenoxy)ethylamino]-2-hydroxypropoxy}carbostyril.hydrochloride
38. 6-[3-(3,4-Dimethoxybenzyl)amino-2-hydroxypropoxy]carbostyril
39. 6-[3-(3-Chlorobenzyl)amino-2-hydroxypropoxy]carbostyril
40. 6-[3-(2-Fluorobenzyl)amino-2-hydroxypropoxy]carbostyril
41. 6-{3-[N-Methyl-N-(2-phenylsulfinylethyl)amino]-2-hydroxypropoxy}carbostyril
42. 6-{3-[N-(2-Hydroxyethyl)-N-(4-fluorobenzyl)]-2-hydroxypropoxy}carbostyril
43. 6-[3-[N-Cyclopropyl-N-benzylamino)-2-hydroxypropoxy]carbostyril
44. 6-[3-[3-Ethoxybenzyl)amino-2-hydroxypropoxy]carbostyril.hydrochloride
45. 6-[3-(3-Phenylthiopropyl)amino-2-hydroxypropoxy]carbostyril
46. 6-{3-(N-(2-Hydroxyethyl)-N-(3-methoxybenzyl)amino]-2-hydroxypropoxy}carbostyril
47. 6-[3-(4-Methylbenzyl)amino-2-hydroxypropoxy]carbostyril
48. 6-[3-(4-Nitrobenzyl)amino-2-hydroxypropoxy]carbostyril
49. 6-[3-Cyanobenzyl)amino-2-hydroxypropoxy]carbostyril 50. 6-[3-{N-Ethyl-N-[2-(3-methoxyphenyl)ethyl]amino]-2-hydroxypropoxy}carbostyril.fumarate
51. 6-[3-(3-Methoxymethoxybenzyl)amino-2-hydroxypropoxy]carbostyril
52. 6-{3-[N-Methyl-N-(2-phenyl-2-hydroxyethyl)amino]-2-hydroxypropoxy}carbostyril
53. 6-[3-(2-Phenoxyethyl)amino-2-hydroxypropoxy]carbostyril.hydrochloride
54. 6-[3-(2,4-Dimethoxybenzyl)amino-2-hydroxypropoxy]carbostyril.hydrochloride
55. 6-[3-(2,3-Dimethoxybenzyl)amino-2-hydroxypropoxy]carbostyril
56. 6-[3-(N-Methyl-N-benzylamino)-2-hydroxypropoxy]-3-cyano-carbostyril
57. 6-{3-[N-Methyl-N-(2-phenylsulfonylethyl)amino]-2-hydroxypropoxy}carbostyril
58. 6-[3-(3,4,5-Trimethoxybenzyl)amino)-2-hydroxypropoxy]carbostyril.hydrochloride
59. 6-[3-{N-Methyl-N-[2-(4-fluorophenyl)sulfinylethyl]amino}-2-hydroxypropoxy]carbostyril
60. 6-[3-{N-Methyl-N-[2-(N-methylanilinocarbonyl)ethyl]amino}-2-hydroxypropoxy]carbostyril
61. 6-[3-{N-(2-Hydroxyethyl)-N-[2-(3-methoxyphenyl)ethyl]amino}-2-hydroxypropoxy]carbostyril
62. 6-{3-[2-(3-Methoxyphenyl)ethyl]amino-2-hydroxypropoxy}carbostyril.hydrochloride
63. 6-{3-[N-(2-Hydroxyethyl)-N-(4-ethoxybenzyl)amino]-2-hydroxypropoxy}carbostyril
64. 6-(3-[N-(4-Ethoxybenzyl)amino]-2-hydroxypropoxy}carbostyril.monohydrochloride
65. 6-{3-[N-Methyl-N-(3-phenylthiopropyl)amino]-2-hydroxypropoxy}carbostyril
66. 6-{3-[N-Methyl-N-(3-phenylsulfinylpropyl)amino]-2-hydroxypropoxy}carbostyril.½ fumarate
67. 6-{3-[N-Methyl-N-(2-phenylsulfinylethyl)amino]-2-hydroxypropoxy}carbostyril.½ fumarate
68. 6-[3-(2-Methoxy-4-methylsulfinylbenzyl)amino-2-hydroxypropoxy]carbostyril.monohydrochloride.½ hydrate
69. 6-{3-[N-Methyl-N-(4-Methoxy-2-pyridylmethyl)amino]-2-hydroxypropoxy}carbostyril.dihydrate
70. 6-{3-[N-Methyl-N-(4-chloro-2-pyridylmethyl)amino]-2-hydroxypropoxy}carbostyril
71. 6-{3-[N-(4-Chloro-2-pyridylmethyl)amino]-2-hydroxypropoxy}carbostyril.monohydrate
72. 6-{3-[N-(2-Thienylmethyl)amino]-2-hydroxypropoxy}carbostyril.monohydrate
73. 6-{3-[N-(4-Methoxy-2-pyridylmethyl)amino]-2-hydroxypropoxy}carbostyril
74. R-(+)-6-[3-(3,4-Dimethoxybenzyl)amino-2-hydroxypropoxy]carbostyril
75. 6-{3-[N-(2-Phenylsulfinylethyl)amino]-2-hydroxypropoxy}carbostyril
76. 6-{3-[N-Methyl-N-(2-pyridyl)amino]-2-hydroxypropoxy}carbostyril
77. 6-[3-{N-Methyl-N-[2-(N-methylanilinc)acetyl]amino]-2-hydroxypropoxy}carbostyril
78. 6-[3-{N-Methyl-N-[3-(N-methylanilino)propionyl]amino}-2-hydroxypropoxy]carbostyril
79. 6-[3-(3-Methoxy-4-methylsulfinylbenzyl)amino-2-hydroxypropoxy]carbostyril.monohydrochloride.2.5 hydrate
80. 6-[3-{N-Methyl-N-[2-(4-methoxyphenyl)sulfonylethyl]amino}-2-hydroxypropoxy]carbostyril
81. 6-[3-{N-Methyl-N-[2-(4-methoxyphenyl)sulfinylethyl]amino}-2-hydroxypropoxy]carbostyril.monooxalate
82. S-(−)-6-[3-(3-Methoxybenzyl)amino-2-hydroxypropoxy]carbostyril
83. R-(+)-6-[3-(3-Methoxybenzyl)amino-2-hydroxypropoxy]carbostyril
84. 6-{3-[N-(3,5-Dimethoxybenzyl)amino]-2-hydroxypropoxy}carbostyril.monohydrochloride
85. 6-[3-{N-Methyl-N-[2-(4-fluorophenyl)sulfinylethyl]amino}-2-hydroxypropoxy]carbostyril
86. 6-[3-{N-Methyl-N-[3-(N-methylanilino)propyl]amino}-2-hydroxypropoxy]carbostyril
87. 6-[3-{N-Methyl-N-[2-(N-methylanilinocarbonyl)ethyl]amino}-2-hydroxypropoxy]carbostyril
88. 6-{3-[N-(3,4,5-Trimethoxybenzyl)amino]-2-hydroxypropoxy}carbostyril.monohydrochloride
89. 6-[3-(4-Methylsulfinylbenzyl)amino-2-hydroxypropoxy]carbostyril
90. 6-{3-[N-Methyl-N-(2-phenylsulfonylethyl)amino]-2-hydroxypropoxy}carbostyril
91. S-(−)-6-[3-(N-Methyl-N-benzylamino)-2-hydroxypropoxy]carbostyril
92. R-(+)-6-[3-(N-Methyl-N-benzylamino)-2-hydroxypropoxy]carbostyril
93. 6-{3-[N-(2-Hydroxyethyl)-N-(3-ethoxybenzyl)amino)-2-hydroxypropoxy}carbostyril
94. R-(+)-6-[3-(4-Fluorobenzylamino)-2-hydroxypropoxy]carbostyril
95. S-(−)-6-[3-(4-Fluorobenzylamino)-2-hydroxypropoxy]carbostyril
96. R-(+)-6-[3-(4-Methoxybenzylamino)-2-hydroxypropoxy)carbostyril.hydrochloride
97. R-(+)-6-[3-(3-Ethoxybenzylamino)-2-hydroxypropoxy]carbostyril.hydrochloride
98. S-(−)-6-[3-(3-Ethoxybenzylamino)-2-hydroxypropoxy]carbostyril.hydrochloride
99. R-(+)-6-[3-(4-Chlorobenzylamino)-2-hydroxypropoxy)carbostyril.hydrochloride
100. S-(−)-6-[3-(4-Chlorobenzylamino)-2-hydroxypropoxy]carbostyril.hydrochloride
101. R-(+)-6-[3-[N-(2-Hydroxyethyl)-N-(4-fluorobenzyl)amino]-2-hydroxypropoxy]carbostyril
102. S-(−)-6-[3-[N-(2-Hydroxyethyl)-N-(4-fluorobenzyl)amino]-2-hydroxypropoxy]carbostyril
103. R-(+)-6-[3-(3,4-Diethyoxybenzylamino)-2-hydroxypropoxy]carbostyril.hydrochloride
104. S-(−)-6-[3-(3,4-Diethyoxybenzylamino)-2-hydroxypropoxy]carbostyril.hydrochloride
105. R-(+)-6-[3-(3,5-Dimethoxybenzylamino)-2-hydroxypropoxy]carbostyril
106. 6-[3-(3,4-Diethoxybenzylamino)-2-hydroxypropoxy]carbostyril.hydrochloride

TABLE 6

| Test Comp. No. | $ED_{30}$ of Amrinone / $ED_{30}$ of Test Comp. | Test Comp. No. | $ED_{30}$ of Amrinone / $ED_{30}$ of Test Comp. |
|---|---|---|---|
| 1 | 2.06 | 29 | 23.4 |
| 2 | 14.9 | 30 | 2.9 |
| 3 | 70.4 | 31 | 5.3 |
| 4 | 41.7 | 32 | 9.4 |
| 5 | 4.1 | 33 | 26.4 |
| 6 | 3.7 | 34 | 6.5 |
| 7 | 3.3 | 35 | 2.9 |
| 8 | 3.9 | 36 | 2.1 |
| 9 | 3.8 | 37 | 26.4 |
| 10 | 7.7 | 38 | 32 |
| 11 | 23.3 | 39 | 127.6 |
| 12 | 2.2 | 40 | 6.7 |
| 13 | 2.4 | 41 | 24.3 |
| 14 | 22.8 | 42 | 14.4 |
| 15 | 3.7 | 43 | 2.3 |
| 16 | 12.7 | 44 | 12.7 |

TABLE 6-continued

| Test Comp. No. | ED30 of Amrinone / ED30 of Test Comp. | Test Comp. No. | ED30 of Amrinone / ED30 of Test Comp. |
|---|---|---|---|
| 17 | 4.3 | 45 | 6.9 |
| 18 | 39.6 | 46 | 10.1 |
| 19 | 8.6 | 47 | 9.2 |
| 20 | 7.4 | 48 | 25.9 |
| 21 | 25.9 | 49 | 8.7 |
| 22 | 52.6 | 50 | 6.6 |
| 23 | 7.9 | 51 | 11.1 |
| 24 | 3.3 | 52 | 11.8 |
| 25 | 24.2 | 53 | 201.6 |
| 26 | 8.7 | 54 | 5.4 |
| 27 | 8.4 | 55 | 6.8 |
| 28 | 6.0 | 56 | 1.25 |
| 57 | 10.1 | 82 | 8.6 |
| 58 | 2.04 | 83 | 8.6 |
| 59 | 2.35 | 84 | 10.83 |
| 60 | 4.28 | 85 | 2.14 |
| 61 | 13.9 | 86 | 5.22 |
| 62 | 2.2 | 87 | 3.93 |
| 63 | 1.26 | 88 | 2.45 |
| 64 | 2.46 | 89 | 0.65 |
| 65 | 10.53 | 90 | 10.06 |
| 66 | 2.14 | 91 | 2.06 |
| 67 | 24.3 | 92 | 2.06 |
| 68 | 0.57 | 93 | 3.33 |
| 69 | 4.51 | 94 | 6.5 |
| 70 | 20.23 | 95 | 6.5 |
| 71 | 195.6 | 96 | 5.3 |
| 72 | 11.66 | 97 | 12.7 |
| 73 | 13.74 | 98 | 12.7 |
| 74 | 64 | 99 | 8.7 |
| 75 | 13.85 | 100 | 8.7 |
| 76 | 104.54 | 101 | 14.4 |
| 77 | 10.64 | 102 | 14.4 |
| 78 | 16.44 | 103 | 64.9 |
| 79 | 2.21 | 104 | 21.6 |
| 80 | 0.84 | 105 | 10.8 |
| 81 | 4.09 | 106 | 49.9 |

| Preparation 1 | |
|---|---|
| Components | Amount in a tablet |
| 6-[3-(2,4-Dimethoxybenzylamino)-2-hydroxypropoxy]carbostyril. hydrochloride | 5 mg |
| Starch | 132 mg |
| Magnesium stearate | 18 mg |
| Lactose | 45 mg |
| Totally | 200 mg |

The above components are tableted in a conventional manner to give tablets containing the above amounts of components in each tablet.

| Preparation 2 | |
|---|---|
| Components | Amount in an injection |
| 6-{3-[N-Methyl-N-{2-[N-methyl-(4-fluoroanilino)]ethyl}amino]-2-hydroxypropoxy}carbostyril | 500 mg |
| Polyethylene glycol (molecular weight: 4,000) | 0.3 mg |
| Sodium chloride | 0.9 g |
| Polyoxyethylene sorbitane monooleate | 0.4 g |
| Sodium metabisulfite | 0.1 g |
| Methyl parabene | 0.18 g |
| Propyl parabene | 0.02 g |
| Distilled water for injection | 100 ml |

The above parabenes, sodium metadisulfite and sodium chloride were dissolved with stirring in the above distilled water at 80° C. The resulting solution was cooled to 40° C., and therein were dissolved the compound of this invention and then polyethylene glycol and polyoxyethylene sorbitane monooleate To the solution was added distilled water for injection so as to make totally 100 ml. The solution was sterilized by filtering with an appropriate filter paper, and then each 1 ml was poured into an ampoule to give an injection.

What is claimed is:

1. A carbostyril compound of the formula:

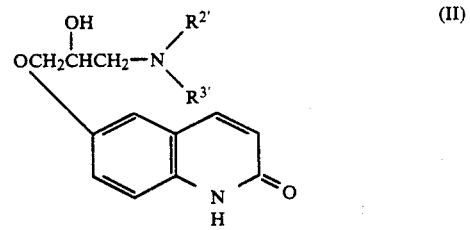

wherein $R^{2'}$ is hydrogen atom, a lower alkyl group being optionally substituted by hydroxy group, a cycloalkyl group, a lower alkenyl group, a phenyl group, a phenyl(lower)alkyl group which has optionally 1 to 3 substituents selected from the group consisting of a lower alkoxy(lower)alkoxy group, a halogen atom, a lower alkoxy group, a nitro group, a lower alkyl group, a cyano group, a lower alkylthio group and a lower alkylsulfinyl group on the phenyl ring and further has optionally a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(lower)alkyl group having optionally 1 to 3 substituents selected from the group consisting of a halogen atom and a lower alkoxy group on the phenyl ring, a phenoxy(lower)alkyl group having optionally 1 to 3 substituents selected from the group consisting of a halogen atom and a lower alkoxy group on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula

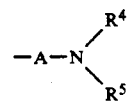

(wherein $R^4$ and $R^5$ are the same or different and are each a lower alkyl group or a phenyl group having optionally 1 to 3 substituents selected from the group consisting of a halogen atom and a lower alkoxy group on the phenyl ring, and A is a lower alkylene group which may optionally be interrupted with oxo group), and $R^{3'}$ is a phenyl(lower)alkyl group which has a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(- lower)alkyl group having optionally 1 to 3 substituents selected from the group consisting of a halogen atom and a lower alkoxy group on the phenyl ring, a phenoxy(lower)alkyl group having 1 to 3 substituents of a halogen atom on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula

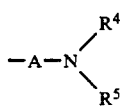

(wherein $R^4$, $R^5$ and A are the same as defined above), or a pharmaceutically acceptable salt thereof 2. A carbostyril compound of the formula:

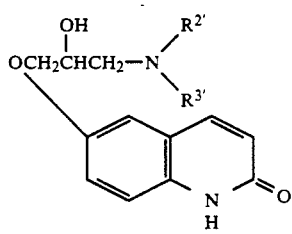

wherein $R^{2'}$ is a lower alkyl group having a hydroxy substituent, and $R^{3'}$ is a phenyl(lower)alkyl group having 1 to 3 substituents selected from the group consisting of a lower alkoxy(lower)alkoxy group, a halogen atom, a nitro group, a lower alkyl group, a cyano group, a lower alkylthio group and a lower alkylsulfinyl group, or a pharmaceutically acceptable salt thereof.

3. A carbostyril compound of the formula:

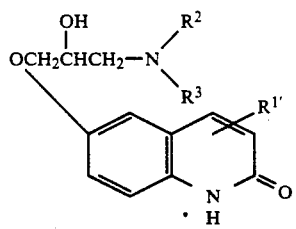

wherein $R^{1'}$ is cyano group, and $R^2$ and $R^3$ are the same or different and are each hydrogen atom, a lower alkyl group being optionally substituted by hydroxy group, a cycloalkyl group, a lower alkenyl group, a phenyl group, a phenyl(lower)alkyl group which has optionally 1 to 3 substituents selected from the group consisting of a lower alkoxy(lower)alkoxy group, a halogen atom, a lower alkoxy group, a nitro group, a lower alkyl group, a cyano group, a lower alkylthio group and a lower alkylsulfinyl group on the phenyl ring and further has optionally a hydroxy substituent on the alkyl moiety, a phenylsulfonyl(lower)alkyl group having optionally 1 to 3 lower alkoxy substituents on the phenyl ring, a phenylthio(lower)alkyl group, a phenylsulfinyl(lower)alkyl group having optionally 1 to 3 substituents selected from the group consisting of a halogen atom and a lower alkoxy group on the phenyl ring, a phenoxy(lower)alkyl group having optionally 1 to 3 substituents selected from the group consisting of a halogen atom and a lower alkoxy group on the phenyl ring, a pyridyl(lower)alkyl group having optionally 1 to 3 substituents selected from the group consisting of a halogen atom and a lower alkoxy group on the pyridine ring, a thienyl(lower)alkyl group, a benzoyl(lower)alkyl group, an anilinothiocarbonyl group, a benzoyl group, a pyridyl group, a phenyl(lower)alkenyl group, or a group of the formula:

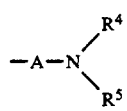

(wherein $R^4$ and $R^5$ are the same or different and are each a lower alkyl group or a phenyl group having optionally 1 to 3 substituents selected from the group consisting of a halogen atom and a lower alkoxy group on the phenyl ring, and A is a lower alkylene group which may optionally be interrupted with oxo group), or a pharmaceutically acceptable salt thereof.

4. The compound according to claim 1, wherein $R^{2'}$ is hydrogen atom or a $C_1$-$C_6$ alkyl group being optionally substituted by hydroxy group, a $C_2$-$C_6$ alkenyl group, a phenyl group, or a phenyl($C_1$-$C_6$)alkyl group which has optionally 1 to 3 substituents selected from the group consisting of a $C_1$-$C_6$ alkoxy($C_1$-$C_6$)alkoxy group, a halogen atom, a $C_1$-$C_6$ alkoxy group, a nitro group, a $C_1$-$C_6$ alkyl group, a cyano group, a $C_1$-$C_6$ alkylthio group and a $C_1$-$C_6$ alkylsulfinyl group on the phenyl ring and further has optionally a hydroxy substituent on the alkyl moiety, or a pharmaceutically acceptable salt thereof.

5. The compound according to claim 1, wherein $R^{2'}$ is a $C_3$-$C_8$ cycloalkyl group, a phenylsulfonyl($C_1$-$C_6$)alkyl group having optionally 1 to 3 $C_1$-$C_6$ alkoxy substituents on the phenyl ring, a phenylthio($C_1$-$C_6$)alkyl group, a phenylsulfinyl($C_1$-$C_6$)alkyl group having optionally 1 to 3 substituents selected from the group consisting of a halogen atom and a $C_1$-$C_6$ alkoxy group on the phenyl ring, a phenoxy($C_1$-$C_6$)alkyl group having optionally 1 to 3 substituents selected from the group consisting of a halogen atom and a $C_1$-$C_6$ alkoxy group on the phenyl ring, a pyridyl($C_1$-$C_6$)alkyl group having optionally 1 to 3 substituents selected from the group consisting of a halogen atom and a $C_1$-$C_6$ alkoxy group on the pyridine ring, a thienyl($C_1$-$C_6$)alkyl group, a benzoyl($C_1$-$C_6$)alkyl group, an anilinothiocarbonyl group, a benzoyl group, a pyridyl group, a phenyl($C_2$-$C_6$)alkenyl group, or a group of the formula:

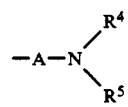

(wherein $R^4$ and $R^5$ are the same or different and are each a $C_1$-$C_6$ alkyl group or a phenyl group having optionally 1 to 3 substituents selected from the group consisting of a halogen atom and a $C_1$-$C_6$ alkoxy group on the phenyl ring, and A is a $C_1$-$C_6$ alkylene group which may optionally be interrupted with oxo group), or a pharmaceutically acceptable salt thereof.

6. The compound according to claim 2, wherein $R^{3'}$ is a phenyl($C_1$-$C_6$)alkyl group which has 1 to 3 substituents of a halogen atom, or a pharmaceutically acceptable salt thereof.

7. The compound according to claim 4, wherein $R^{3'}$ is a phenylsulfinyl($C_1$-$C_6$)alkyl group having optionally 1 to 3 substituents selected from the group consisting of a halogen atom and a $C_1$-$C_6$ alkoxy group on the phenyl ring, or a pharmaceutically acceptable salt thereof.

8. The compound according to claim 4, wherein $R^{3'}$ is a phenyl($C_1$-$C_6$)alkyl group having a hydroxy substituent on the alkyl moiety, a phenylsulfonyl($C_1$-$C_6$)alkyl group having optionally 1 to 3 $C_1$-$C_6$ alkoxy substituents on the phenyl ring, a phenylthio($C_1$-$C_6$)alkyl group, a phenoxy($C_1$-$C_6$)alkyl group having 1 to 3 substituents of a halogen atom on the phenyl ring, a pyridyl($C_1$-$C_6$)alkyl group having optionally 1 to 3 substituents selected from the on the pyridine ring, a thienyl($C_1$-$C_6$)alkyl group, a benzoyl($C_1$-$C_6$)alkyl group, an anilinothiocarbonyl group, a benzoyl group, a pyridyl group, a phenyl($C_2$-$C_6$)alkenyl group, or a group of the formula:

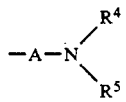

(wherein $R^4$ and $R^5$ are the same or different and are each a $C_1$-$C_6$ alkyl group or a phenyl group having optionally 1 to 3 substituents selected from the group consisting of a halogen atom and a $C_1$-$C_6$ alkoxy group on the phenyl ring, and A is a $C_1$-$C_6$ alkylene group which may optionally be interrupted with oxo group), or a pharmaceutically acceptable salt thereof.

9. The compound according to claim 5, wherein $R^{3'}$ is a phenylsulfinyl($C_1$-$C_6$)alkyl group having optionally 1 to 3 substituents selected from the group consisting of a halogen atom and a $C_1$-$C_6$ alkoxy group on the phenyl ring, or a pharmaceutical acceptable salt thereof.

10. The compound according to claim 7, wherein substituted by hydroxy group, and $R^{3'}$ is a phenylsulfinyl($C_1$-$C_6$)alkyl group having optionally 1 to 3 substituents selected from the group consisting of a halogen atom and a $C_1$-$C_6$ alkoxy group on the phenyl ring, or a pharmaceutically acceptable salt thereof.

11. A pharmaceutical composition for the prophylaxis or treatment of heart diseases which comprises an effective amount of a carbostyril derivative as set forth in claim 1 in admixture with a pharmaceutically acceptable carrier or diluent.

12. A pharmaceutical composition for the prophylaxis or treatment of heart diseases which comprises an effective amount of a carbostyril derivative as set forth in claim 2 in admixture with a pharmaceutically acceptable carrier or diluent.

13. A pharmaceutical composition for the prophylaxis and treatment of heart diseases which comprises an effective amount of a carbostyril derivative se set forth in claim 3 in admixture with a pharmaceutically acceptable carrier or diluent.

14. The composition according to claim 11, wherein the active compound is 6-[3-[N-(2-hydroxyethyl)-N-(4-fluorobenzyl)amino]-2-hydroxypropoxy]carbostyril.

15. The composition according to claim 11, wherein the active compound is 6-[3-[N-methyl-N-(2-phenylsulfinylethyl)amino]-2-hydroxypropoxy]carbostyril.

* * * * *